United States Patent [19]

Isogai et al.

[11] Patent Number: 5,773,272

[45] Date of Patent: Jun. 30, 1998

[54] **D-AMINO ACID OXIDASE OF *F. SOLANI* AND METHODS FOR ITS RECOMBINANT PRODUCTION**

[75] Inventors: Takao Isogai, Tsukuba; Hiroki Ono, Osaka; Hitoshi Kojo, Tsukuba, all of Japan

[73] Assignee: Fujisawa Pharmaceutical Co., Ltd., Osaka, Japan

[21] Appl. No.: 536,277

[22] Filed: Sep. 29, 1995

Related U.S. Application Data

[63] Continuation of Ser. No. 361,708, Dec. 22, 1994, Pat. No. 5,602,016, which is a continuation of Ser. No. 126,891, Sep. 27, 1993, abandoned, which is a continuation of Ser. No. 3,854, Jan. 11, 1993, abandoned, which is a continuation of Ser. No. 418,524, Oct. 10, 1989, abandoned.

[30] Foreign Application Priority Data

Oct. 13, 1988 [JP] Japan .................................. 63-260332

[51] Int. Cl.[6] ........................... C12N 09/20; C12N 15/35; C12N 15/79; C12P 35/00
[52] U.S. Cl. ........................... 435/189; 435/47; 435/69.1; 435/252.3; 435/252.33; 435/320.1; 536/23.2
[58] Field of Search ........................... 435/189, 47, 69.1, 435/252.3, 252.33, 320.1; 536/23.2

[56] References Cited

U.S. PATENT DOCUMENTS

| | | | |
|---|---|---|---|
| 3,950,662 | 4/1976 | Matsuda et al. | 435/51 |
| 4,652,639 | 3/1987 | Stabinsky | 435/91.52 |
| 4,806,478 | 2/1989 | Stahl | 435/180 |
| 5,208,155 | 5/1993 | Mosbach et al. | 435/191 |
| 5,602,016 | 2/1997 | Isogai et al. | 435/189 |

FOREIGN PATENT DOCUMENTS

| | | |
|---|---|---|
| 57-018879 | 4/1982 | Japan . |
| 62-262944 | 11/1987 | Japan . |
| 63-071180 | 3/1988 | Japan . |
| 63-074488 | 4/1988 | Japan . |
| 1272769 | 3/1972 | United Kingdom . |

OTHER PUBLICATIONS

Fujii, T., et al., Chemical Abstracts, vol. 85, No. 7, Abstract No. 63080b at p. 567, 1976.
Tsuda, M., et al., Chemical Abstracts, vol. 71, Abstract No. 10538m at p. 92, 1969.
Chiari, D. F., Biochimica et Biophysica Acta, vol. 165, "D–Amino–acid oxidase in Fusarium", pp. 127–133, 1968.
Tsunasawa, S., et al., 1984, Methods in Enzymology, vol. 106, pp. 165–170, 1984.
Szwajcer, E., et al, Biotechnology Letters, vol. 7, pp. 1–7, 1985.
Fortkamp, E., et al., DNA, vol. 5, pp. 511–517, 1986.
Leonil, J., et al., Journal of Chromatography, vol. 347, pp. 316–319, 1985.
Kubicek–Pranz, E. M., Journal of Applied Biochemistry, vol. 7, pp. 104–113, 1985.
Swenson, R. P., et al., The Journal of Biological Chemistry, vol. 257, pp. 8817–8823, 1982.
Ronchi, S., et al., The Journal of Biological Chemistry, vol. 257, pp. 8824–8834, 1982.
Ren, K., et al., Acta Microbiologica Sinica, vol. 26, pp. 242–249, 1986.
Deshpande, A., et al., Biotechnology Techniques, vol. 1, pp. 55–58, 1987.
Jacobs, P., et al., Gene, vol 59, pp. 55–61, 1987.
Fukui, K., et al., Biochemistry, vol. 26, pp. 3612–3618, 1987.
Momoi, K., et al., FEBS Letters, vol. 238, pp. 180–184, 1988.
Prokop, A., et al., p. 54 in Recombinant DNA Technology and Applications, McGraw–Hill, Inc., publishers, 1991.

*Primary Examiner*—Charles L. Patterson, Jr.
*Assistant Examiner*—William W. Moore
*Attorney, Agent, or Firm*—Oblon, Spivak, McClelland, Maier & Neustadt, P.C.

[57] ABSTRACT

D-amino acid oxidase (DAO) originated from *Fusarium solani* M-0718, a DNA compound encoding the oxidase, expression vectors containing said DNA compound are provided. *Esherichia coli* transformants capable of producing recombinant DAO in high level are also provided.

4 Claims, 21 Drawing Sheets

FIG. 6(1)

```
BamIII  SmaI              vector
  ↓    ↓ 10      20  ← | 30         40         50         60
GGATCCCCGG GCGAGCTGGG GGGGAGCGAC TTGAATTTAG CGAAAAGAAC TTGTCAACCA
                                                       AatII
       70         80         90        100        110   ↓  120
CAATC[ATG]TC CAACACAATC GTCGTCGTTG GTGCCGGTGT CATTGGCTTG ACGTCGGCCT
                                             BalI
      130        140        150        160  ↓  170        180
TGTTGCTCTC CAAGAACAAG GGCAACAAGA TCACCGTCGT GGCCAAGCAC ATGCCCGGCG
                                                    Synthetic DNA probe
                                            NcoI
      190        200        210        220  ↓ 230        240
ACTATGACGT TGAATACGCC TCGCCTTTTG CTGGTGCCAA CCACTCCCCC ATGGCGACGG
AP-6 and AP-7
                                                           AvaII
      250        260        270        280        290  ↓ 300
AAGAGAGCAG CGAATGGGAA CGTCGCACTT GGTACGAGTT TAAGAGACTG GTCGAGGAGG
                                                    Synthetic DNA
SauI
  ↓   310        320        330        340        350        360
TCCCTGAGGC CGGTGTTCAT TTCCAGAAGT CTCGCATCCA GAGGCGCAAT GTGGACACTG
probe AP-3

370        380        390        400        410        420
AAAAGGCGCA GAGGTCTGGT TTCCCAGACG CCCTCTTCTC GAAAGAACCC TGGTTCAAGA
                                                         Synthetic 430        440        450        460        470        480
ACATGTTTGA GGACTTCCGT GAGCAGCACC CTAGCGAGGT CATCCCCGGT TACGACTCTG
DNA probe AP-9

490        500        510        520        530        540
GCTGCGAGTT CACATCGGTG TGCATCAACA CGGCCATCTA CCTCCCCTGG CTCCTCGGCC 550        560        570        580        590        600
AGTGCATCAA GAATGGCGTC ATCGTCAAGC GCGCCATCCT CAACGACATT AGCGAGGCCA
```

FIG. 6(2)

```
         610        620        630        640        650        660
    AGAAGCTGAG CCACGCGGGC AAGACGCCCA ATATCATCGT CAACGCCACG GGTCTCGGCT
                                              Bbel  HaeII
                                            Nco I NarI
         670        680        690 ↓     ↓ |  700        710        720
    CCTACAAGCT GGGCGGTGTC GAGGACAAGA CCATGGCGCC TGCGCGGGGA CAGATTGTGG Mst I
       ↓ 730       740        750        760        770        780
    TTGTGCGCAA CGAGAGCAGC CCCATGCTCC TCACTTCAGG TGTCGAGGAC GGCGGTGCTG
                                  Pvu II
         790        800       ↓ 810       820        830        840
    ATGTCATGTA CTTGATGCAG CGAGCAGCTG GCGGTGGCAC CATCCTGGGC GGTACCTACG
                                                              Nru I
         850        860        870      ↓ 880        890        900
    ACGTTGGCAA CTGGGAGTCT CAGCCAGACC CCAACATCGC GAATCGCATC ATGCAGCGCA 910        920        930        940        950        960
    TCGTCGAGGT GCGGCCCGAG ATTGCCAACG GCAAGGGCGT CAAGGGGCTG AGCGTGATCC
                    SphI XmaIII
         970       | | 980      990       1000       1010       1020
    GACACGCCGT CGGCATGCGG CCGTGGCGAA AGGACGGAGT CAGGATCGAG GAGGAGAAGC
                                                              BstEII
        1030       1040       1050       1060      ↓ 1070       1080
    TGGATGATGA GACTTGGATC GTGCACAACT ACGGACACTC TGGATGGGGT TACCAGGGTT 1090       1100       1110       1120       1130       1140
    CGTATGGTTG TGCTGAGAAT GTAGTCCAGT TGGTTGACAA GGTCGGCAAG GCGGCCAAGT
                                Stu I
        1150       1160 ↓      1170       1180       1190       1200
    CTAAGCTG|TA G|TTGAAAAGG CCTGAATGAG TAATAGTAAT TGGATATTGG AAATACCGTA 1210       1220       1230       1240       1250       1260
    TTTGCCCTCG AAAAAAAAAA AAAAAAAAAA AAAAAAAAAA AAGTACCTTC TGAGGCGGAA
                                 SacI SmaI BamHI   | →vector
        1270       1280      ↓ 1290 ↓    ↓
    AGAACCAGCC GGATCAXTTC GAGCTCGCCC GGGGATCC
```

FIG. 7(1)

```
         10         20         30         40         50         60
ATGTCCAACACAATCGTCGTCGTTGGTGCCGGTGTCATTGGCTTGACGTCGGCCTTGTTG
MetSerAsnThrIleValValValGlyAlaGlyValIleGlyLeuThrSerAlaLeuLeu 70         80         90        100        110        120
CTCTCCAAGAACAAGGGCAACAAGATCACCGTCGTGGCCAAGCACATGCCCGGCGACTAT
LeuSerLysAsnLysGlyAsnLysIleThrValValAlaLysHisMetProGlyAspTyr 130        140        150        160        170        180
GACGTTGAATACGCCTCGCCTTTTGCTGGTGCCAACCACTCCCCCATGGCGACGGAAGAG
AspValGluTyrAlaSerProPheAlaGlyAlaAsnHisSerProMetAlaThrGluGlu 190        200        210        220        230        240
AGCAGCGAATGGGAACGTCGCACTTGGTACGAGTTTAAGAGACTGGTCGAGGAGGTCCCT
SerSerGluTrpGluArgArgThrTrpTyrGluPheLysArgLeuValGluGluValPro 250        260        270        280        290        300
GAGGCCGGTGTTCATTTCCAGAAGTCTCGCATCCAGAGGCGCAATGTGGACACTGAAAAG
GluAlaGlyValHisPheGlnLysSerArgIleGlnArgArgAsnValAspThrGluLys 310        320        330        340        350        360
GCGCAGAGGTCTGGTTTCCCAGACGCCCTCTTCTCGAAAGAACCCTGGTTCAAGAACATG
AlaGlnArgSerGlyPheProAspAlaLeuPheSerLysGluProTrpPheLysAsnMet 370        380        390        400        410        420
TTTGAGGACTTCCGTGAGCAGCACCCTAGCGAGGTCATCCCCGGTTACGACTCTGGCTGC
PheGluAspPheArgGluGlnHisProSerGluValIleProGlyTyrAspSerGlyCys 430        440        450        460        470        480
GAGTTCACATCGGTGTGCATCAACACGGCCATCTACCTCCCCTGGCTCCTCGGCCAGTGC
GluPheThrSerValCysIleAsnThrAlaIleTyrLeuProTrpLeuLeuGlyGlnCys 490        500        510        520        530        540
ATCAAGAATGGCGTCATCGTCAAGCGCGCCATCCTCAACGACATTAGCGAGGCCAAGAAG
IleLysAsnGlyValIleValLysArgAlaIleLeuAsnAspIleSerGluAlaLysLys 550        560        570        580        590        600
CTGAGCCACGCGGGCAAGACGCCCAATATCATCGTCAACGCCACGGGTCTCGGCTCCTAC
LeuSerHisAlaGlyLysThrProAsnIleIleValAsnAlaThrGlyLeuGlySerTyr
```

FIG. 7(2)

```
         610       620       630       640       650       660
AAGCTGGGCGGTGTCGAGGACAAGACCATGGCGCCTGCGCGGGGACAGATTGTGGTTGTG
LysLeuGlyGlyValGluAspLysThrMetAlaProAlaArgGlyGlnIleValValVal 670       680       690       700       710       720
CGCAACGAGAGCAGCCCCATGCTCCTCACTTCAGGTGTCGAGGACGGCGGTGCTGATGTC
ArgAsnGluSerSerProMetLeuLeuThrSerGlyValGluAspGlyGlyAlaAspVal 730       740       750       760       770       780
ATGTACTTGATGCAGCGAGCAGCTGGCGGTGGCACCATCCTGGGCGGTACCTACGACGTT
MetTyrLeuMetGlnArgAlaAlaGlyGlyGlyThrIleLeuGlyGlyThrTyrAspVal 790       800       810       820       830       840
GGCAACTGGGAGTCTCAGCCAGACCCCAACATCGCGAATCGCATCATGCAGCGCATCGTC
GlyAsnTrpGluSerGlnProAspProAsnIleAlaAsnArgIleMetGlnArgIleVal 850       860       870       880       890       900
GAGGTGCGGCCCGAGATTGCCAACGGCAAGGGCGTCAAGGGGCTGAGCGTGATCCGACAC
GluValArgProGluIleAlaAsnGlyLysGlyValLysGlyLeuSerValIleArgHis 910       920       930       940       950       960
GCCGTCGGCATGCGGCCGTGGCGAAAGGACGGAGTCAGGATCGAGGAGGAGAAGCTGGAT
AlaValGlyMetArgProTrpArgLysAspGlyValArgIleGluGluGluLysLeuAsp 970       980       990      1000      1010      1020
GATGAGACTTGGATCGTGCACAACTACGGACACTCTGGATGGGGTTACCAGGGTTCGTAT
AspGluThrTrpIleValHisAsnTyrGlyHisSerGlyTrpGlyTyrGlnGlySerTyr 1030      1040      1050      1060      1070      1080
GGTTGTGCTGAGAATGTAGTCCAGTTGGTTGACAAGGTCGGCAAGGCGGCCAAGTCTAAG
GlyCysAlaGluAsnValValGlnLeuValAspLysValGlyLysAlaAlaLysSerLys

CTGTAG
Leu***
```

FIG. 8(1)

10
SerAsnThrIleValValValGlyAlaGlyValIleGlyLeuThrSerAlaLeuLeu 20                              30
LeuSerLysAsnLysGlyAsnLysIleThrValValAlaLysHisMetProGlyAspTyr
                                          AP-6 and AP-7

40                              50
AspValGluTyrAlaSerProPheAlaGlyAlaAsnHisSerProMetAlaThrGluGlu 60                              70
SerSerGluTrpGluArgArgThrTrpTyrGluPheLysArgLeuValGluGluValPro
                                          AP-3

80                              90
GluAlaGlyValHisPheGlnLysSerArgIleGlnArgArgAsnValAspThrGluLys 100                             110
AlaGlnArgSerGlyPheProAspAlaLeuPheSerLysGluProTrpPheLysAsnMet
                                     AP-2              AP-9

120                             130
PheGluAspPheArgGluGlnHisProSerGluValIleProGlyTyrAspSerGlyCys 140                             150
GluPheThrSerValCysIleAsnThrAlaIleTyrLeuProTrpLeuLeuGlyGlnCys 160                             170
IleLysAsnGlyValIleValLysArgAlaIleLeuAsnAspIleSerGluAlaLysLys
                                AP-1

180                             190
LeuSerHisAlaGlyLysThrProAsnIleIleValAsnAlaThrGlyLeuGlySerTyr
                       AP-5

200                             210
LysLeuGlyGlyValGluAspLysThrMetAlaProAlaArgGlyGlnIleValValVal
                            AP-8

220                             230
ArgAsnGluSerSerProMetLeuLeuThrSerGlyValGluAspGlyAlaAspVal

FIG. 8(2)

240 250
MetTyrLeuMetGlnArgAlaAlaGlyGlyGlyThrIleLeuGlyGlyThrTyrAspVal 260 270
GlyAsnTrpGluSerGlnProAspProAsnIleAlaAsnArgIleMetGlnArgIleVal 280 290
GluValArgProGluIleAlaAsnGlyLysGlyValLys<u>GlyLeuSerValIleArgHis</u>
                                              AP-4
300 330
<u>AlaValGlyMet</u>ArgProTrpArgLysAspGlyValArgIleGluGluGluLysLeuAsp 320 330
AspGluThrTrpIleValHisAsnTyrGlyHisSerGlyTrpGlyTyrGlnGlySerTyr 340 350
GlyCysAlaGluAsnValValGlnLeuValAspLysValGlyLysAlaAlaLysSerLys

360
Leu

FIG.9(1)

F. solani M-0718
Trigonopsis variabilis

10
SerAsnThrIleValValGlyAlaGlyValIleGlyLeuThrSerAlaLeu  Leu
         AlaLya  · Ile  ·   Ala  ·  ·  Thr  ·   Gln ·

20                                            30
LeuSerLysAsnLysGlyAsnLysIleThrValValAlaLysHisMetProGlyAspTyr
         ·    Arg  ·  HisGluVal  · Ile    SerGluPheThr  ·    · Leu 40                                            50
AspValGluTyrAlaSerProPheAlaGlyAlaAsnHisSerPrIMetAlaThrGluGlu
SerIleGly · Thr  ·  · Thr  ·  ·  ·  ·  · TrpLeuThrPheTyrAspGlyGly 60                                            70
SerSerGluTrpGluArgArgThrTrpTyrGluPheLysArgLeuValGluGluVal   Pro
LysLeuAlaAspTyrAspalaVal ser  · ProIleLeu  ·  GluLeuAlaArgSerSer ·

80                                            90
GluAlaGlyValHisPheGlnLysSerArgIleGlyArgArgAsnValAspThrGluLys
              IleArgLeuIleAsnGln  ·  SerHisValLeuLysArg  · LeuPro 100                                           110
AlaGlnArgSerGlyPheProAspAlaLeuPheSerLysGluProTrpPheLysAsnMet
LeuGluGlyAlaMetSerAlaIleCysGlnArgAsn  ·  ·  ·  ·  ·  ·  · Thr

FIG. 9(2)

```
120             130
PheGluAsp   PheArgGluGlnHisProSerGluValIleProGlyTyrAspSerGlyCys
Val    · Ser    ·     IleIleGluAspArgSerArgIleVal His  ·  AspGluAlaTyrLeu 140             150
GluPheThrSerValCysIleAsnThrAlaIleTyrLeuProTrpLeuLeuGlyGlnCys
Val    · Arg    ·     His  ·   GlyVal  ·   Asn    ·  MetSer ·

160             160
IleLysAsnGlyValIleVal      LysArgAlaIleLeuAsnAspIleSerGluAlaLysLys
LeuSerLeu ·  AlaThr ·  Val   ·   ArgVal   ·   His  ·  LysAsp  ·  Asn 180             190
LeuSerHisAla       GlyLysThrProAsnIleIleValAsnAlaThrGlyLeuGlySerTyr
 ·   Leu ·  SerSer  ·  SerArg  ·   AspVal  ·   ·   CysSer  ·   PheAlaArg 200             210
LysLeuGlyValGluAspLysThrMetAlaProAlaArgGlyGlnIleValVal    Val
Phe   ·   ·   ·   ·   ·   ·   ·   Lys · Tyr · Ile  ·   ·   ·   Leu  ·

220             230
ArgAsnGluSerSerPro    MetLeuLeuThrSerGlyValGluAspGlyAlaAspVal
 ·   ·   ·   ·   ·   Leu · Phe · AlaSerPhe · SerThrProGluLysGluAsnGluAsp
```

FIG. 9(3)

```
240                                 250
MetTyrLeuMetGlnArgAlaAlaGlyGlyGlyThr   IleLeuGlyGlyThrTyrAspVal
GluAla · TyrIleMetThrArgPheAsp ·  · Ser · Ile ·  · CysPheGlnPro 260                                 270
GlyAsnTrpGluSerGlnProAspProAsnIleAlaAsnargIleMetGlnArgIleVal
Asn ·  · Ser · Glu ·  ·  · SerLeuThrHis ·  · LeuSer · AlaLeu 280                                 290
GluValArg   ProGluIleAlaAsnGlyLys   GluValLysGlyLeuSer   ValIleArgHis
Asp  · Phe ·  · LeuThr ·  · Asp · Pro ·  · AspIle ·  · Glu 300                                 310
AlaValGlyMetArgProTrpArgLysAspGlyValArgIleGluGluGluLysLeuAsp
Cys ·  · His ·  · Gly · GluGly · Pro · Val · Leu ·  · IlePro 320                                 330
AspGluThrtrpIleValHisAsnTyrGlyHisSerGlyTrpGlyTyrGlnGlySerTyr
GlyValGlyPheVal ·  ·  ·  · AlaAla · Ala ·  · Ser ·  ·

340                                 350
GlyCysAla   GluAsnValValGlnLeuValAspLysValGlyLysAlaAlaLysSerLys
 · Met · Asp · Ala · SerTyr   · GluArgAlaLeuThrArgProAsn

360
Leu
 ·
```

```
    |  A'      |          C    |         E    |         G    |
AATTCGCCGA CATCATAACG GTTCTGGCAA ATATTCTGAA ATGAGCTGTT GACAATTAAT
    GCGGCT GTAGTATTGC CAAGACCGTT TATAAGACTT TACTCGACAA CTGTTAATTA
    |     B'    |         D    |         F    |       H      |

|    I    |         K    |    M'   |
CATCGAACTA GTTAACTAGT ACGCAAGTTC ACGTAAAAAG GGTAG
GTAGCTTGAT CAATTGATCA TGCGTTCAAG TGCATTTTTC CCATAGC
         |    J    |         L    |    N'   |
```

FIG. 14
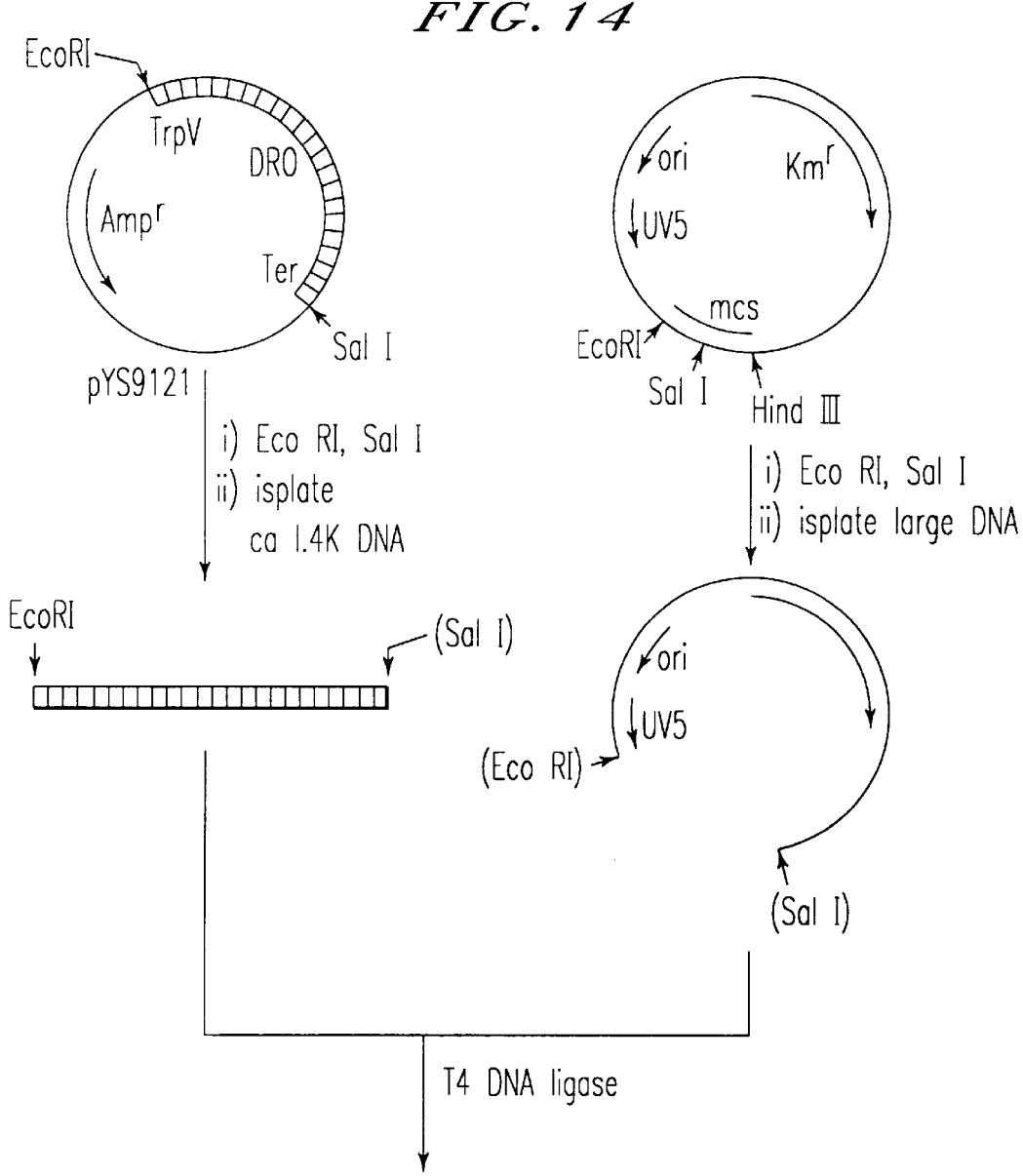
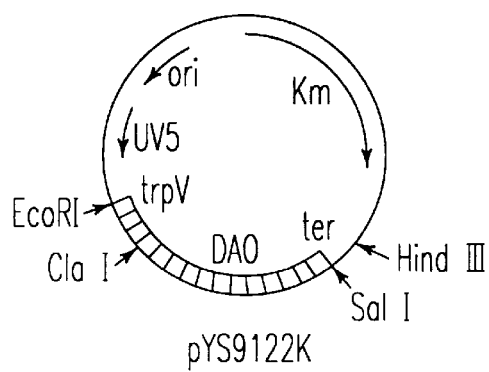

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 1298 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

-continued

| | | | | | |
|---|---|---|---|---|---|
| GGATCCCCGG | GCGAGCTGGG | GGGGAGCGAC | TTGAATTTAG | CGAAAAGAAC | TTGTCAACCA | 60 |
| CAATCATGTC | CAACACAATC | GTCGTCGTTG | GTGCCGGTGT | CATTGGCTTG | ACGTCGGCCT | 120 |
| TGTTGCTCTC | CAAGAACAAG | GGCAACAAGA | TCACCGTCGT | GGCCAAGCAC | ATGCCCGGCG | 180 |
| ACTATGACGT | TGAATACGCC | TCGCCTTTTG | CTGGTGCCAA | CCACTCCCCC | ATGGCGACGG | 240 |
| AAGAGAGCAG | CGAATGGGAA | CGTCGCACTT | GGTACGAGTT | TAAGAGACTG | GTCGAGGAGG | 300 |
| TCCCTGAGGC | CGGTGTTCAT | TTCCAGAAGT | CTCGCATCCA | GAGGCGCAAT | GTGGACACTG | 360 |
| AAAAGGCGCA | GAGGTCTGGT | TTCCCAGACG | CCCTCTTCTC | GAAAGAACCC | TGGTTCAAGA | 420 |
| ACATGTTTGA | GGACTTCCGT | GAGCAGCACC | CTAGCGAGGT | CATCCCCGGT | TACGACTCTG | 480 |
| GCTGCGAGTT | CACATCGGTG | TGCATCAACA | CGGCCATCTA | CCTCCCCTGG | CTCCTCGGCC | 540 |
| AGTGCATCAA | GAATGGCGTC | ATCGTCAAGC | GCGCCATCCT | CAACGACATT | AGCGAGGCCA | 600 |
| AGAAGCTGAG | CCACGCGGGC | AAGACGCCCA | ATATCATCGT | CAACGCCACG | GGTCTCGGCT | 660 |
| CCTACAAGCT | GGGCGGTGTC | GAGGACAAGA | CCATGGCGCC | TGCGCGGGGA | CAGATTGTGG | 720 |
| TTGTGCGCAA | CGAGAGCAGC | CCCATGCTCC | TCACTTCAGG | TGTCGAGGAC | GGCGGTGCTG | 780 |
| ATGTCATGTA | CTTGATGCAG | CGAGCAGCTG | GCGGTGGCAC | CATCCTGGGC | GGTACCTACG | 840 |
| ACGTTGGCAA | CTGGGAGTCT | CAGCCAGACC | CCAACATCGC | GAATCGCATC | ATGCAGCGCA | 900 |
| TCGTCGAGGT | GCGGCCCGAG | ATTGCCAACG | GCAAGGGCGT | CAAGGGGCTG | AGCGTGATCC | 960 |
| GACACGCCGT | CGGCATGCGG | CCGTGGCGAA | AGGACGGAGT | CAGGATCGAG | GAGGAGAAGC | 1020 |
| TGGATGATGA | GACTTGGATC | GTGCACAACT | ACGGACACTC | TGGATGGGGT | TACCAGGGTT | 1080 |
| CGTATGGTTG | TGCTGAGAAT | GTAGTCCAGT | TGGTTGACAA | GGTCGGCAAG | GCGGCCAAGT | 1140 |
| CTAAGCTGTA | GTTGAAAAGG | CCTGAATGAG | TAATAGTAAT | TGGATATTGG | AAATACCGTA | 1200 |
| TTTGCCCTCG | AAAAAAAAAA | AAAAAAAAAA | AAAAAAAAAA | AAGTACCTTC | TGAGGCGGAA | 1260 |
| AGAACCAGCC | GGATCANTTC | GAGCTCGCCC | GGGGATCC | | | 1298 |

( 2 ) INFORMATION FOR SEQ ID NO:2:

( i ) SEQUENCE CHARACTERISTICS:
        ( A ) LENGTH: 1086 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1083

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| ATG | TCC | AAC | ACA | ATC | GTC | GTC | GTT | GGT | GCC | GGT | GTC | ATT | GGC | TTG | ACG | 48 |
| Met | Ser | Asn | Thr | Ile | Val | Val | Val | Gly | Ala | Gly | Val | Ile | Gly | Leu | Thr | |
| 1 | | | | 5 | | | | | 10 | | | | | 15 | | |
| TCG | GCC | TTG | TTG | CTC | TCC | AAG | AAC | AAG | GGC | AAC | AAG | ATC | ACC | GTC | GTG | 96 |
| Ser | Ala | Leu | Leu | Leu | Ser | Lys | Asn | Lys | Gly | Asn | Lys | Ile | Thr | Val | Val | |
| | | | 20 | | | | | 25 | | | | | 30 | | | |
| GCC | AAG | CAC | ATG | CCC | GGC | GAC | TAT | GAC | GTT | GAA | TAC | GCC | TCG | CCT | TTT | 144 |
| Ala | Lys | His | Met | Pro | Gly | Asp | Tyr | Asp | Val | Glu | Tyr | Ala | Ser | Pro | Phe | |
| | | | 35 | | | | | 40 | | | | | 45 | | | |
| GCT | GGT | GCC | AAC | CAC | TCC | CCC | ATG | GCG | ACG | GAA | GAG | AGC | AGC | GAA | TGG | 192 |
| Ala | Gly | Ala | Asn | His | Ser | Pro | Met | Ala | Thr | Glu | Glu | Ser | Ser | Glu | Trp | |
| | | | 50 | | | | | 55 | | | | | 60 | | | |
| GAA | CGT | CGC | ACT | TGG | TAC | GAG | TTT | AAG | AGA | CTG | GTC | GAG | GAG | GTC | CCT | 240 |
| Glu | Arg | Arg | Thr | Trp | Tyr | Glu | Phe | Lys | Arg | Leu | Val | Glu | Glu | Val | Pro | |
| 65 | | | | 70 | | | | | 75 | | | | | 80 | | |

```
GAG GCC GGT GTT CAT TTC CAG AAG TCT CGC ATC CAG AGG CGC AAT GTG      288
Glu Ala Gly Val His Phe Gln Lys Ser Arg Ile Gln Arg Arg Asn Val
                85                  90                  95

GAC ACT GAA AAG GCG CAG AGG TCT GGT TTC CCA GAC GCC CTC TTC TCG      336
Asp Thr Glu Lys Ala Gln Arg Ser Gly Phe Pro Asp Ala Leu Phe Ser
            100                 105                 110

AAA GAA CCC TGG TTC AAG AAC ATG TTT GAG GAC TTC CGT GAG CAG CAC      384
Lys Glu Pro Trp Phe Lys Asn Met Phe Glu Asp Phe Arg Glu Gln His
        115                 120                 125

CCT AGC GAG GTC ATC CCC GGT TAC GAC TCT GGC TGC GAG TTC ACA TCG      432
Pro Ser Glu Val Ile Pro Gly Tyr Asp Ser Gly Cys Glu Phe Thr Ser
    130                 135                 140

GTG TGC ATC AAC ACG GCC ATC TAC CTC CCC TGG CTC CTC GGC CAG TGC      480
Val Cys Ile Asn Thr Ala Ile Tyr Leu Pro Trp Leu Leu Gly Gln Cys
145                 150                 155                 160

ATC AAG AAT GGC GTC ATC GTC AAG CGC GCC ATC CTC AAC GAC ATT AGC      528
Ile Lys Asn Gly Val Ile Val Lys Arg Ala Ile Leu Asn Asp Ile Ser
                165                 170                 175

GAG GCC AAG AAG CTG AGC CAC GCG GGC AAG ACG CCC AAT ATC ATC GTC      576
Glu Ala Lys Lys Leu Ser His Ala Gly Lys Thr Pro Asn Ile Ile Val
            180                 185                 190

AAC GCC ACG GGT CTC GGC TCC TAC AAG CTG GGC GGT GTC GAG GAC AAG      624
Asn Ala Thr Gly Leu Gly Ser Tyr Lys Leu Gly Gly Val Glu Asp Lys
        195                 200                 205

ACC ATG GCG CCT GCG CGG GGA CAG ATT GTG GTT GTG CGC AAC GAG AGC      672
Thr Met Ala Pro Ala Arg Gly Gln Ile Val Val Val Arg Asn Glu Ser
    210                 215                 220

AGC CCC ATG CTC CTC ACT TCA GGT GTC GAG GAC GGC GGT GCT GAT GTC      720
Ser Pro Met Leu Leu Thr Ser Gly Val Glu Asp Gly Gly Ala Asp Val
225                 230                 235                 240

ATG TAC TTG ATG CAG CGA GCA GCT GGC GGT GGC ACC ATC CTG GGC GGT      768
Met Tyr Leu Met Gln Arg Ala Ala Gly Gly Gly Thr Ile Leu Gly Gly
                245                 250                 255

ACC TAC GAC GTT GGC AAC TGG GAG TCT CAG CCA GAC CCC AAC ATC GCG      816
Thr Tyr Asp Val Gly Asn Trp Glu Ser Gln Pro Asp Pro Asn Ile Ala
            260                 265                 270

AAT CGC ATC ATG CAG CGC ATC GTC GAG GTG CGG CCC GAG ATT GCC AAC      864
Asn Arg Ile Met Gln Arg Ile Val Glu Val Arg Pro Glu Ile Ala Asn
        275                 280                 285

GGC AAG GGC GTC AAG GGG CTG AGC GTG ATC CGA CAC GCC GTC GGC ATG      912
Gly Lys Gly Val Lys Gly Leu Ser Val Ile Arg His Ala Val Gly Met
    290                 295                 300

CGG CCG TGG CGA AAG GAC GGA GTC AGG ATC GAG GAG GAG AAG CTG GAT      960
Arg Pro Trp Arg Lys Asp Gly Val Arg Ile Glu Glu Glu Lys Leu Asp
305                 310                 315                 320

GAT GAG ACT TGG ATC GTG CAC AAC TAC GGA CAC TCT GGA TGG GGT TAC     1008
Asp Glu Thr Trp Ile Val His Asn Tyr Gly His Ser Gly Trp Gly Tyr
                325                 330                 335

CAG GGT TCG TAT GGT TGT GCT GAG AAT GTA GTC CAG TTG GTT GAC AAG     1056
Gln Gly Ser Tyr Gly Cys Ala Glu Asn Val Val Gln Leu Val Asp Lys
            340                 345                 350

GTC GGC AAG GCG GCC AAG TCT AAG CTG TAG                             1086
Val Gly Lys Ala Ala Lys Ser Lys Leu
        355                 360
```

( 2 ) INFORMATION FOR SEQ ID NO:3:

( i ) SEQUENCE CHARACTERISTICS:
        ( A ) LENGTH: 361 amino acids
        ( B ) TYPE: amino acid
        ( D ) TOPOLOGY: linear (i i) MOLECULE TYPE: protein (x i) SEQUENCE DESCRIPTION: SEQ ID NO:3:

| Met | Ser | Asn | Thr | Ile | Val | Val | Val | Gly | Ala | Gly | Val | Ile | Gly | Leu | Thr |
| 1 | | | | 5 | | | | | 10 | | | | | 15 | |

| Ser | Ala | Leu | Leu | Leu | Ser | Lys | Asn | Lys | Gly | Asn | Lys | Ile | Thr | Val | Val |
| | | | 20 | | | | | 25 | | | | | 30 | | |

| Ala | Lys | His | Met | Pro | Gly | Asp | Tyr | Asp | Val | Glu | Tyr | Ala | Ser | Pro | Phe |
| | | | 35 | | | | | 40 | | | | | 45 | | |

| Ala | Gly | Ala | Asn | His | Ser | Pro | Met | Ala | Thr | Glu | Glu | Ser | Ser | Glu | Trp |
| | | 50 | | | | | 55 | | | | | 60 | | | |

| Glu | Arg | Arg | Thr | Trp | Tyr | Glu | Phe | Lys | Arg | Leu | Val | Glu | Val | Pro |
| 65 | | | | | 70 | | | | | 75 | | | | | 80 |

| Glu | Ala | Gly | Val | His | Phe | Gln | Lys | Ser | Arg | Ile | Gln | Arg | Arg | Asn | Val |
| | | | | 85 | | | | | 90 | | | | | 95 | |

| Asp | Thr | Glu | Lys | Ala | Gln | Arg | Ser | Gly | Phe | Pro | Asp | Ala | Leu | Phe | Ser |
| | | | 100 | | | | | 105 | | | | | 110 | | |

| Lys | Glu | Pro | Trp | Phe | Lys | Asn | Met | Phe | Glu | Asp | Phe | Arg | Glu | Gln | His |
| | | 115 | | | | | 120 | | | | | 125 | | | |

| Pro | Ser | Glu | Val | Ile | Pro | Gly | Tyr | Asp | Ser | Gly | Cys | Glu | Phe | Thr | Ser |
| | | 130 | | | | | 135 | | | | | 140 | | | |

| Val | Cys | Ile | Asn | Thr | Ala | Ile | Tyr | Leu | Pro | Trp | Leu | Leu | Gly | Gln | Cys |
| 145 | | | | | 150 | | | | | 155 | | | | | 160 |

| Ile | Lys | Asn | Gly | Val | Ile | Val | Lys | Arg | Ala | Ile | Leu | Asn | Asp | Ile | Ser |
| | | | | 165 | | | | | 170 | | | | | 175 | |

| Glu | Ala | Lys | Lys | Leu | Ser | His | Ala | Gly | Lys | Thr | Pro | Asn | Ile | Ile | Val |
| | | | 180 | | | | | 185 | | | | | 190 | | |

| Asn | Ala | Thr | Gly | Leu | Gly | Ser | Tyr | Lys | Leu | Gly | Gly | Val | Glu | Asp | Lys |
| | | 195 | | | | | 200 | | | | | 205 | | | |

| Thr | Met | Ala | Pro | Ala | Arg | Gly | Gln | Ile | Val | Val | Val | Arg | Asn | Glu | Ser |
| | | 210 | | | | | 215 | | | | | 220 | | | |

| Ser | Pro | Met | Leu | Leu | Thr | Ser | Gly | Val | Glu | Asp | Gly | Gly | Ala | Asp | Val |
| 225 | | | | | 230 | | | | | 235 | | | | | 240 |

| Met | Tyr | Leu | Met | Gln | Arg | Ala | Ala | Gly | Gly | Gly | Thr | Ile | Leu | Gly | Gly |
| | | | | 245 | | | | | 250 | | | | | 255 | |

| Thr | Tyr | Asp | Val | Gly | Asn | Trp | Glu | Ser | Gln | Pro | Asp | Pro | Asn | Ile | Ala |
| | | | 260 | | | | | 265 | | | | | 270 | | |

| Asn | Arg | Ile | Met | Gln | Arg | Ile | Val | Glu | Val | Arg | Pro | Glu | Ile | Ala | Asn |
| | | | 275 | | | | | 280 | | | | | 285 | | |

| Gly | Lys | Gly | Val | Lys | Gly | Leu | Ser | Val | Ile | Arg | His | Ala | Val | Gly | Met |
| | | 290 | | | | | 295 | | | | | 300 | | | |

| Arg | Pro | Trp | Arg | Lys | Asp | Gly | Val | Arg | Ile | Glu | Glu | Lys | Leu | Asp |
| 305 | | | | | 310 | | | | | 315 | | | | | 320 |

| Asp | Glu | Thr | Trp | Ile | Val | His | Asn | Tyr | Gly | His | Ser | Gly | Trp | Gly | Tyr |
| | | | | 325 | | | | | 330 | | | | | 335 | |

| Gln | Gly | Ser | Tyr | Gly | Cys | Ala | Glu | Asn | Val | Val | Gln | Leu | Val | Asp | Lys |
| | | | 340 | | | | | 345 | | | | | 350 | | |

| Val | Gly | Lys | Ala | Ala | Lys | Ser | Lys | Leu |
| | | 355 | | | | | 360 | |

(2) INFORMATION FOR SEQ ID NO:4:

(i) SEQUENCE CHARACTERISTICS:
        (A) LENGTH: 360 amino acids
        (B) TYPE: amino acid (D) TOPOLOGY: linear (ii) MOLECULE TYPE: protein (vi) ORIGINAL SOURCE:
    (A) ORGANISM: Fusarium solani
    (B) STRAIN: M-0718

(xi) SEQUENCE DESCRIPTION: SEQ ID NO:4:

```
Ser Asn Thr Ile Val Val Val Gly Ala Gly Val Ile Gly Leu Thr Ser
 1               5                  10                  15
Ala Leu Leu Leu Ser Lys Asn Lys Gly Asn Lys Ile Thr Val Val Ala
             20                  25                  30
Lys His Met Pro Gly Asp Tyr Asp Val Glu Tyr Ala Ser Pro Phe Ala
         35                  40                  45
Gly Ala Asn His Ser Pro Met Ala Thr Glu Glu Ser Ser Glu Trp Glu
     50                  55                  60
Arg Arg Thr Trp Tyr Glu Phe Lys Arg Leu Val Glu Glu Val Pro Glu
 65                  70                  75                  80
Ala Gly Val His Phe Gln Lys Ser Arg Ile Gln Arg Arg Asn Val Asp
                 85                  90                  95
Thr Glu Lys Ala Gln Arg Ser Gly Phe Pro Asp Ala Leu Phe Ser Lys
             100                 105                 110
Glu Pro Trp Phe Lys Asn Met Phe Glu Asp Phe Arg Glu Gln His Pro
         115                 120                 125
Ser Glu Val Ile Pro Gly Tyr Asp Ser Gly Cys Glu Phe Thr Ser Val
     130                 135                 140
Cys Ile Asn Thr Ala Ile Tyr Leu Pro Trp Leu Leu Gly Gln Cys Ile
145                 150                 155                 160
Lys Asn Gly Val Ile Val Lys Arg Ala Ile Leu Asn Asp Ile Ser Glu
                 165                 170                 175
Ala Lys Lys Leu Ser His Ala Gly Lys Thr Pro Asn Ile Ile Val Asn
             180                 185                 190
Ala Thr Gly Leu Gly Ser Tyr Lys Leu Gly Gly Val Glu Asp Lys Thr
         195                 200                 205
Met Ala Pro Ala Arg Gly Gln Ile Val Val Val Arg Asn Glu Ser Ser
210                 215                 220
Pro Met Leu Leu Thr Ser Gly Val Glu Asp Gly Gly Ala Asp Val Met
225                 230                 235                 240
Tyr Leu Met Gln Arg Ala Ala Gly Gly Gly Thr Ile Leu Gly Gly Thr
                 245                 250                 255
Tyr Asp Val Gly Asn Trp Glu Ser Gln Pro Asp Pro Asn Ile Ala Asn
             260                 265                 270
Arg Ile Met Gln Arg Ile Val Glu Val Arg Pro Glu Ile Ala Asn Gly
         275                 280                 285
Lys Gly Val Lys Gly Leu Ser Val Ile Arg His Ala Val Gly Met Arg
     290                 295                 300
Pro Trp Arg Lys Asp Gly Val Arg Ile Glu Glu Glu Lys Leu Asp Asp
305                 310                 315                 320
Glu Thr Trp Ile Val His Asn Tyr Gly His Ser Gly Trp Gly Tyr Gln
                 325                 330                 335
Gly Ser Tyr Gly Cys Ala Glu Asn Val Val Gln Leu Val Asp Lys Val
             340                 345                 350
Gly Lys Ala Ala Lys Ser Lys Leu
         355                 360
```

(2) INFORMATION FOR SEQ ID NO:5:

(i) SEQUENCE CHARACTERISTICS:
     (A) LENGTH: 356 amino acids
     (B) TYPE: amino acid
     (D) TOPOLOGY: linear (ii) MOLECULE TYPE: protein (vi) ORIGINAL SOURCE:
     (A) ORGANISM: Trigonopsis variabilis (xi) SEQUENCE DESCRIPTION: SEQ ID NO:5:

```
Ser Ala Lys Ile Val Val Ile Gly Ala Gly Val Ala Gly Leu Thr Thr
 1               5                  10                  15

Ala Leu Gln Leu Leu Arg Lys Gly His Glu Val Thr Ile Val Ser Glu
             20                  25                  30

Phe Thr Pro Gly Asp Leu Ser Ile Gly Tyr Thr Ser Pro Trp Ala Gly
         35                  40                  45

Ala Asn Trp Leu Thr Phe Tyr Asp Gly Gly Lys Leu Ala Asp Tyr Asp
     50                  55                  60

Ala Val Ser Tyr Pro Ile Leu Arg Glu Leu Ala Arg Ser Ser Pro Glu
 65                  70                  75                  80

Ala Gly Ile Arg Leu Ile Asn Gln Arg Ser His Val Leu Lys Arg Asp
                 85                  90                  95

Leu Pro Lys Leu Glu Gly Ala Met Ser Ala Ile Cys Gln Arg Asn Pro
            100                 105                 110

Trp Phe Lys Asn Thr Val Asp Ser Phe Glu Ile Ile Glu Asp Arg Ser
        115                 120                 125

Arg Ile Val His Asp Asp Glu Ala Tyr Leu Val Glu Phe Arg Ser Val
    130                 135                 140

Cys Ile His Thr Gly Val Tyr Leu Asn Trp Leu Met Ser Gln Cys Leu
145                 150                 155                 160

Ser Leu Gly Ala Thr Val Val Lys Arg Arg Val Asn His Ile Lys Asp
                165                 170                 175

Ala Asn Leu Leu His Ser Ser Gly Ser Arg Pro Asp Val Ile Val Asn
            180                 185                 190

Cys Ser Gly Leu Phe Ala Arg Phe Leu Gly Gly Val Glu Asp Lys Lys
        195                 200                 205

Met Tyr Pro Ile Arg Gly Gln Val Val Leu Val Arg Asn Ser Leu Pro
    210                 215                 220

Phe Met Ala Ser Phe Ser Ser Thr Pro Glu Lys Glu Asn Glu Asp Glu
225                 230                 235                 240

Ala Leu Tyr Ile Met Thr Arg Phe Asp Gly Thr Ser Ile Ile Gly Gly
                245                 250                 255

Cys Phe Gln Pro Asn Asn Trp Ser Ser Glu Pro Asp Pro Ser Leu Thr
            260                 265                 270

His Arg Ile Leu Ser Arg Ala Leu Asp Arg Phe Pro Glu Leu Thr Lys
        275                 280                 285

Asp Gly Pro Leu Asp Ile Val Arg Glu Cys Val Gly His Arg Pro Gly
    290                 295                 300

Arg Glu Gly Gly Pro Arg Val Glu Leu Glu Lys Ile Pro Gly Val Gly
305                 310                 315                 320

Phe Val Val His Asn Tyr Gly Ala Ala Gly Ala Gly Tyr Gln Ser Ser
                325                 330                 335

Tyr Gly Met Ala Asp Glu Ala Val Ser Tyr Val Glu Arg Ala Leu Thr
            340                 345                 350
```

Arg Pro Asn Leu
355

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Arg Ala Ile Leu Asn Asp Ile Ser Glu Ala Lys
1               5                   10

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Glu Pro Xaa Phe Lys
1               5

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Arg Leu Val Glu Glu Val Pro Glu Ala Gly Val His Phe Gln Lys
1               5                   10                  15

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Gly Leu Ser Val Ile Arg Xaa Ala Val Gly Met
1               5                   10

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Thr Pro Asn Ile Ile Val Asn Ala Thr Gly Leu Gly Ser Tyr Lys
1               5                   10                  15

( 2 ) INFORMATION FOR SEQ ID NO:11:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:11:

```
His Met Pro Gly Asp Tyr Asp Val Glu Tyr Ala Ser
1               5                   10
```

( 2 ) INFORMATION FOR SEQ ID NO:12:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:12:

```
His Met Pro Gly Asp Tyr Asp Val Glu Tyr Ala Ser Xaa Phe Ala
1               5                   10                  15
```

( 2 ) INFORMATION FOR SEQ ID NO:13:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:13:

```
Thr Met Ala Pro Ala Arg Gly Gln Ile Val Val Arg Asn Glu Ser
1               5                   10                  15

Ser Pro Met Leu Leu
                20
```

( 2 ) INFORMATION FOR SEQ ID NO:14:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:14:

```
Asn Met Phe Glu Asp Phe Xaa Glu Gln
1               5
```

( 2 ) INFORMATION FOR SEQ ID NO:15:

( i ) SEQUENCE CHARACTERISTICS:
    ( A ) LENGTH: 36 base pairs
    ( B ) TYPE: nucleic acid
    ( C ) STRANDEDNESS: unknown
    ( D ) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:15:

GAGGAGGTYC CTGAGGCYGG YGTYCACTTC CAGAAG    36

( 2 ) INFORMATION FOR SEQ ID NO:16:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:16:

```
Glu  Glu  Val  Pro  Glu  Ala  Gly  Val  His  Phe  Gln  Lys
 1                    5                        10
```

( 2 ) INFORMATION FOR SEQ ID NO:17:

( i ) SEQUENCE CHARACTERISTICS:
    ( A ) LENGTH: 18 base pairs
    ( B ) TYPE: nucleic acid
    ( C ) STRANDEDNESS: unknown
    ( D ) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:17:

```
AAYATGTTCG AGGAYTTC                                                       18
```

( 2 ) INFORMATION FOR SEQ ID NO:18:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:18:

```
Asn  Met  Phe  Glu  Asp  Phe
 1                    5
```

( 2 ) INFORMATION FOR SEQ ID NO:19:

( i ) SEQUENCE CHARACTERISTICS:
    ( A ) LENGTH: 26 base pairs
    ( B ) TYPE: nucleic acid
    ( C ) STRANDEDNESS: unknown
    ( D ) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:19:

```
ATGCCTGGYG AYTACGAYGT YGAGTA                                              26
```

( 2 ) INFORMATION FOR SEQ ID NO:20:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:20:

```
Met  Pro  Gly  Asp  Tyr  Asp  Val  Glu  Tyr
 1                    5
```

( 2 ) INFORMATION FOR SEQ ID NO:21:

( i ) SEQUENCE CHARACTERISTICS:
    ( A ) LENGTH: 5 amino acids
    ( B ) TYPE: amino acid (D) TOPOLOGY: linear (ii) MOLECULE TYPE: peptide (xi) SEQUENCE DESCRIPTION: SEQ ID NO:21:

Glu Pro Trp Phe Lys
1               5

(2) INFORMATION FOR SEQ ID NO:22:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:22:

Gly Leu Ser Val Ile Arg His Ala Val Gly Met
1               5                   10

(2) INFORMATION FOR SEQ ID NO:23:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (xi) SEQUENCE DESCRIPTION: SEQ ID NO:23:

His Met Pro Gly Asp Tyr Asp Val Glu Tyr Ala Ser Pro Phe Ala
1               5                   10                  15

(2) INFORMATION FOR SEQ ID NO:24:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (xi) SEQUENCE DESCRIPTION: SEQ ID NO:24:

Asn Met Phe Glu Asp Phe Arg Glu Gln
1               5

(2) INFORMATION FOR SEQ ID NO:25:

(i) SEQUENCE CHARACTERISTICS:
    (A) LENGTH: 96 base pairs
    (B) TYPE: nucleic acid
    (C) STRANDEDNESS: unknown
    (D) TOPOLOGY: linear (ii) MOLECULE TYPE: DNA (genomic)

(xi) SEQUENCE DESCRIPTION: SEQ ID NO:25:

AGCTTACTCC CCATCCCCCT GTTGACAATT AATCATCGGC TCGTATAATG TGTGGAATTG        60

TGAGCGGATA ACAATTTCAC ACAGGAAACA GGATCC                                  96

(2) INFORMATION FOR SEQ ID NO:26:

(i) SEQUENCE CHARACTERISTICS:
    (A) LENGTH: 58 base pairs
    (B) TYPE: nucleic acid
    (C) STRANDEDNESS: both
    (D) TOPOLOGY: linear (ii) MOLECULE TYPE: Other nucleic acid;
    (A) DESCRIPTION: synthetic DNA (xi) SEQUENCE DESCRIPTION: SEQ ID NO:26:

GATCCAATCA TGTCCAACAC AATCGTCGTC GTTGGTGCCG GTGTCATTGG CTTGACGT    58

(2) INFORMATION FOR SEQ ID NO:27:

(i) SEQUENCE CHARACTERISTICS:
        (A) LENGTH: 50 base pairs
        (B) TYPE: nucleic acid
        (C) STRANDEDNESS: both
        (D) TOPOLOGY: linear (ii) MOLECULE TYPE: Other nucleic acid;
        (A) DESCRIPTION: synthetic DNA (xi) SEQUENCE DESCRIPTION: SEQ ID NO:27:

CAAGCCAATG ACACCGGCAC CAACGACGAC GATTGTGTTG GACATGATTG    50

(2) INFORMATION FOR SEQ ID NO:28:

(i) SEQUENCE CHARACTERISTICS:
        (A) LENGTH: 56 base pairs
        (B) TYPE: nucleic acid
        (C) STRANDEDNESS: both
        (D) TOPOLOGY: linear (ii) MOLECULE TYPE: Other nucleic acid;
        (A) DESCRIPTION: synthetic DNA (xi) SEQUENCE DESCRIPTION: SEQ ID NO:28:

CGATAAAATG TCCAACACAA TCGTCGTCGT TGGTGCCGGT GTCATTGGCT TGACGT    56

(2) INFORMATION FOR SEQ ID NO:29:

(i) SEQUENCE CHARACTERISTICS:
        (A) LENGTH: 50 base pairs
        (B) TYPE: nucleic acid
        (C) STRANDEDNESS: both
        (D) TOPOLOGY: linear (ii) MOLECULE TYPE: Other nucleic acid;
        (A) DESCRIPTION: synthetic DNA (xi) SEQUENCE DESCRIPTION: SEQ ID NO:29:

CAAGCCAATG ACACCGGCAC CAACGACGAC GATTGTGTTG GACATTTTAT    50

(2) INFORMATION FOR SEQ ID NO:30:

(i) SEQUENCE CHARACTERISTICS:
        (A) LENGTH: 12 base pairs
        (B) TYPE: nucleic acid
        (C) STRANDEDNESS: both
        (D) TOPOLOGY: linear (ii) MOLECULE TYPE: Other nucleic acid;
        (A) DESCRIPTION: synthetic DNA (xi) SEQUENCE DESCRIPTION: SEQ ID NO:30:

AATTCGCCGA CA    12

(2) INFORMATION FOR SEQ ID NO:31:

(i) SEQUENCE CHARACTERISTICS:
        (A) LENGTH: 16 base pairs
        (B) TYPE: nucleic acid
        (C) STRANDEDNESS: both
        (D) TOPOLOGY: linear ( i i ) MOLECULE TYPE: Other nucleic acid;
    ( A ) DESCRIPTION: synthetic DNA ( x i ) SEQUENCE DESCRIPTION: SEQ ID NO:31:

CGTTATGATG TCGGCG                                                                        16

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:32:

TCATAACGGT TCTGGC                                                                        16

( 2 ) INFORMATION FOR SEQ ID NO:33:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:33:

GAATATTTGC CAGAAC                                                                        16

( 2 ) INFORMATION FOR SEQ ID NO:34:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:34:

AAATATTCTG AAATGA                                                                        16

( 2 ) INFORMATION FOR SEQ ID NO:35:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: linear ( i i ) MOLECULE TYPE: Other nucleic acid;
        ( A ) DESCRIPTION: synthetic DNA ( x i ) SEQUENCE DESCRIPTION: SEQ ID NO:35:

TCAACAGCTC ATTTCA                                                                        16

( 2 ) INFORMATION FOR SEQ ID NO:36:

( i ) SEQUENCE CHARACTERISTICS:
        ( A ) LENGTH: 16 base pairs
        ( B ) TYPE: nucleic acid
        ( C ) STRANDEDNESS: both
        ( D ) TOPOLOGY: linear ( i i ) MOLECULE TYPE: Other nucleic acid;
( A ) DESCRIPTION: synthetic DNA ( x i ) SEQUENCE DESCRIPTION: SEQ ID NO:36:

GCTGTTGACA ATTAAT 16

( 2 ) INFORMATION FOR SEQ ID NO:37:

( i ) SEQUENCE CHARACTERISTICS:
( A ) LENGTH: 16 base pairs
( B ) TYPE: nucleic acid
( C ) STRANDEDNESS: both
( D ) TOPOLOGY: linear ( i i ) MOLECULE TYPE: Other nucleic acid;
( A ) DESCRIPTION: synthetic DNA ( x i ) SEQUENCE DESCRIPTION: SEQ ID NO:37:

GTTCGATGAT TAATTG 16

( 2 ) INFORMATION FOR SEQ ID NO:38:

( i ) SEQUENCE CHARACTERISTICS:
( A ) LENGTH: 16 base pairs
( B ) TYPE: nucleic acid
( C ) STRANDEDNESS: both
( D ) TOPOLOGY: linear ( i i ) MOLECULE TYPE: Other nucleic acid;
( A ) DESCRIPTION: synthetic DNA ( x i ) SEQUENCE DESCRIPTION: SEQ ID NO:38:

CATCGAACTA GTTAAC 16

( 2 ) INFORMATION FOR SEQ ID NO:39:

( i ) SEQUENCE CHARACTERISTICS:
( A ) LENGTH: 16 base pairs
( B ) TYPE: nucleic acid
( C ) STRANDEDNESS: both
( D ) TOPOLOGY: linear ( i i ) MOLECULE TYPE: Other nucleic acid;
( A ) DESCRIPTION: synthetic DNA ( x i ) SEQUENCE DESCRIPTION: SEQ ID NO:39:

GCGTACTAGT TAACTA 16

( 2 ) INFORMATION FOR SEQ ID NO:40:

( i ) SEQUENCE CHARACTERISTICS:
( A ) LENGTH: 16 base pairs
( B ) TYPE: nucleic acid
( C ) STRANDEDNESS: both
( D ) TOPOLOGY: linear ( i i ) MOLECULE TYPE: Other nucleic acid;
( A ) DESCRIPTION: synthetic DNA ( x i ) SEQUENCE DESCRIPTION: SEQ ID NO:40:

TAGTACGCAA GTTCAC 16

( 2 ) INFORMATION FOR SEQ ID NO:41:

( i ) SEQUENCE CHARACTERISTICS:
( A ) LENGTH: 16 base pairs
( B ) TYPE: nucleic acid
( C ) STRANDEDNESS: both
( D ) TOPOLOGY: linear (   i i   ) MOLECULE TYPE: Other nucleic acid;
          ( A ) DESCRIPTION: synthetic DNA (   x i   ) SEQUENCE DESCRIPTION: SEQ ID NO:41:

CTTTTTACGT GAACTT                                                                                       1 6

( 2 ) INFORMATION FOR SEQ ID NO:42:

( i ) SEQUENCE CHARACTERISTICS:
              ( A ) LENGTH: 13 base pairs
              ( B ) TYPE: nucleic acid
              ( C ) STRANDEDNESS: both
              ( D ) TOPOLOGY: linear (   i i   ) MOLECULE TYPE: Other nucleic acid;
              ( A ) DESCRIPTION: synthetic DNA (   x i   ) SEQUENCE DESCRIPTION: SEQ ID NO:42:

GTAAAAAGGG TAT                                                                                          1 3

( 2 ) INFORMATION FOR SEQ ID NO:43:

( i ) SEQUENCE CHARACTERISTICS:
              ( A ) LENGTH: 16 amino acids
              ( B ) TYPE: amino acid
              ( D ) TOPOLOGY: linear (   i i   ) MOLECULE TYPE: peptide ( v ) FRAGMENT TYPE: N-terminal (   i x   ) FEATURE:
              ( A ) NAME/KEY: Modified-site
              ( B ) LOCATION: 1
              ( D ) OTHER INFORMATION: /note= "fMet"

(   x i   ) SEQUENCE DESCRIPTION: SEQ ID NO:43:

Met  Ser  Asn  Thr  Ile  Val  Val  Val  Gly  Ala  Gly  Val  Ile  Gly  Leu  Thr
1                        5                       10                      15

( 2 ) INFORMATION FOR SEQ ID NO:44:

( i ) SEQUENCE CHARACTERISTICS:
              ( A ) LENGTH: 15 amino acids
              ( B ) TYPE: amino acid
              ( D ) TOPOLOGY: linear (   i i   ) MOLECULE TYPE: peptide ( v ) FRAGMENT TYPE: N-terminal (   x i   ) SEQUENCE DESCRIPTION: SEQ ID NO:44:

Ser  Asn  Thr  Ile  Val  Val  Val  Gly  Ala  Gly  Val  Ile  Gly  Leu  Xaa
1                   5                        10                      15

D-AMINO ACID OXIDASE OF *F. SOLANI* AND METHODS FOR ITS RECOMBINANT PRODUCTION

This is a Continuation of application Ser. No. 08/361,708 filed on Dec. 22, 1994, and issued as U.S. Pat. No. 5,602,016 on Feb. 11, 1997, which is a continuation of Ser. No. 08/126,891, filed Sep. 27, 1993, abandoned; which is a continuation of Ser. No. 08/003,854, filed Jan. 11, 1993, abandoned; which is a continuation of Ser. No. 07/418,524, filed Oct. 10, 1989, abandoned.

This invention relates to a novel D-amino acid oxidase (DAO). More particularly, it relates to DAO originated from *Fusarium solani* M0718, a DNA encoding thereof, expression vectors containing said DNA, microorganisms transformed with said expression vectors, and the production of recombinant DAO by culturing said transformants.

DAO is an enzyme which catalyze oxidative deamination of D-amino acids. DAOs have been found widely in microorganisms as well as in tissues of animals including vertebrates. On the other hand, it has already been known that the mycelia of a DAO-producing strain, *Fusarium solani* M-0718 or its processed materials convert cephalosporin C (CC) into 7-β-(5-carboxy-5-oxopentanamido) cephalosporanic acid (keto-AD-7ACA) and a portion of the products can be reacted with hydrogen peroxide which is formed as a by-product in the above reaction to give 7-β-(4-carboxy butanamido)-cephalosporanic acid (GL-7ACA). [See, Japanese Patent Publication (Kokoku) No. 18879/1982]. In this connection, the *Fusarium solani* M-0718 has been available from Fermentation Research Institute, Agency of Industrial Science and Technology, 1–3, Higashi 1 chome, Tsukuba-shi, Ibaraki-ken, Japan, under the deposit No. FERM BP-2688 prior to the filing date of the basic Japanese Patent Application No. 260332/1988. Furthermore, the same organism was additionally deposited with the said depository under the deposit No. FERM BP-2619 on Oct. 2, 1989 according to the stipulations of the Budapest Treaty. GL-7ACA can be converted into 7-aminocephalosporanic acid (7ACA) in the presence of GL-7ACA acylase. 7ACA is one of the most popular starting materials for the synthesis of commercially useful cephem antibiotics, such as cefazolin and the like. The reaction schema of enzymatic synthesis of 7ACA from CC via keto-AD-7ACA and GL-7ACA is illustrated below.

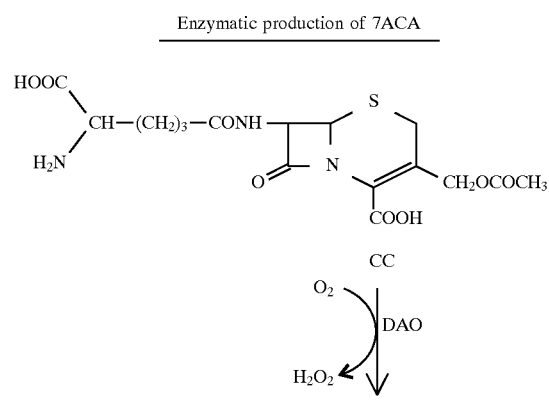

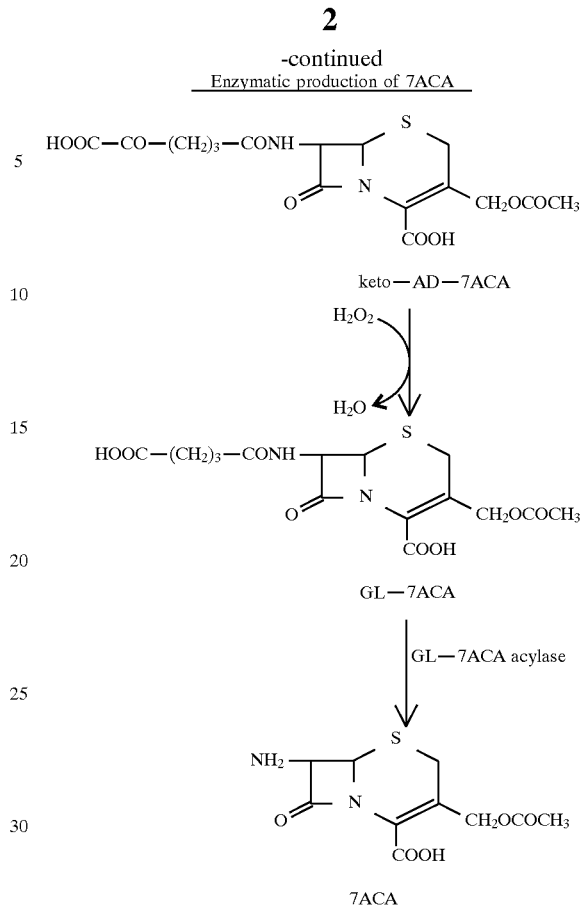

The final product 7ACA is a significantly important starting material for producing cephem antibiotics with a widely ranged antibacterial spectrum. Therefore, it would be highly desirable to establish an efficient process for producing 7ACA from CC to make an advancement in the production and development of cephem antibiotics. The production of 7ACA from CC has been generally performed using complicated chemical synthesis. Recently, bioreactor-system which utilizes enzymes derived from organisms as the catalysts have been developed. This system takes advantage of the high substrate specificity of enzymes, namely, DAO and GL-7ACA acylase. In order to apply said system to the production of 7ACA, it is needed to obtain specific enzymes in a sufficient amount.

This invention is aimed to establish an efficient means for producing a large amounts of DAO or its active derivative applicable to the bio-reactor-system or direct expression system for producing 7ACA.

A gene encoding DAO originated from *Trigonopsis variabilis* has been cloned (Japanese Patent No. 262994/1987 and its amino acid sequence has been disclosed (see, FIG. 9). To the contrary, DAO from *F. solani* has not been purified and a gene encording the same has not been cloned before the present invention.

The inventors purified DAO from a strain of *F. solani*, more specifically, *F. solani* M-0718, determined the nucleotide sequence of the DNA encoding DAO and cloned the DAO gene. The cloning was accomplished by isolating mRNA encoding DAO from mycelia of *F. solani*, constructing cDNA libraries from mRNAs, probing said libraries, and cloning a DNA encoding DAO as will be further explained below. Once the DNA sequence has been identified and cloned, the preparation of microorganisms capable of producing DAO can be easily accomplished using recombinant DNA technology, such as the construction of expression vectors comprising said DNA, transformation of microorganisms with expression vectors, cultivation of the transformants in a medium under a suitable conditions for the expression of DAO, and isolation of the products having the activity of DAO.

Thus, this invention provides DAO originated from *F. solani*. More specifically, this invention provides DAO of *F. solani* having the amino acid sequence shown in the accompanying FIG. 7.

This invention also provides a recombinant DNA encoding DAO of *F. solani* and expression vectors comprising said DNA.

This invention further provides a novel microorganism transformed by the expression vector of the invention and capable of producing DAO in high level.

This invention further provides a method for preparing DAO by culturing a transformant of the invention in an aqueous nutrient medium containing assimilable carbon or nitrogen sources under aerobic conditions.

This invention also provides the recombinant DAO products produced by the method of present invention.

For the purpose of the invention, as disclosed and claimed herein, the following terms are defined as below.

DAO: D-amino acid oxidase, an enzyme which catalyze oxidative deamination of D-amino acid to 2-oxo acid. The DAO of the invention is originally isolated and purified from *F. solani* and reactive on CC to give keto-AD-7ACA and GL-7ACA. For the purpose of the invention, the term "DAO" refers to both of naturally occurring DAO and recombinant DAO produced by the method of invention. The DNA sequence encoding DAO is now determined, it is easy to obtain active derivatives of native DAO within the scope of the present invention by conventional methods, such as site specific change. Therefore, the term "DAO" also include active derivatives of DAO which can be derived by conventional methods in the art.

DAO gene: structural gene of DAO, or DNA encoding DAO.

$Amp^R$: ampicilline-resistant phenotype or gene conferring the same.

$Km^R$: kanamycin-resistant phenotype or gene conferring the same.

$Cm^R$: chloramphenicol-resistant phenotype or gene conferring the same.

DESCRIPTION OF THE DRAWINGS

FIG. 6 is a DNA sequence (SEQ ID NO: 1) of 1.3 kb BamHI restriction fragment of plasmid pCFS3.

FIG. 7 is a DNA sequence of DAO (SEQ ID NO: 2) and deduced amino acid sequence (SEQ ID NO: 3).

FIG. 8 shows the comparison between deduced amino acid sequence of DAO (SEQ ID NO: 3) and those of 9 peptide fragments AP-1 to AP-9 isolated by reversed phase HPLC.

FIG. 9 shows the comparison between the amino acid sequence of DAO from *F. solani* M-0718 (SEQ ID NO: 4) and that from *T. variabilis* (SEQ ID NO: 5). In the sequence for the DAO of *T.variabilis*, amino acids identical to those of *F. solani* are represented by dots.

FIG. 14 is a schematic illustration of the construction protocol for the plasmid pYS9122K.

DETAILED DESCRIPTION OF THE INVENTION

Figure 1:
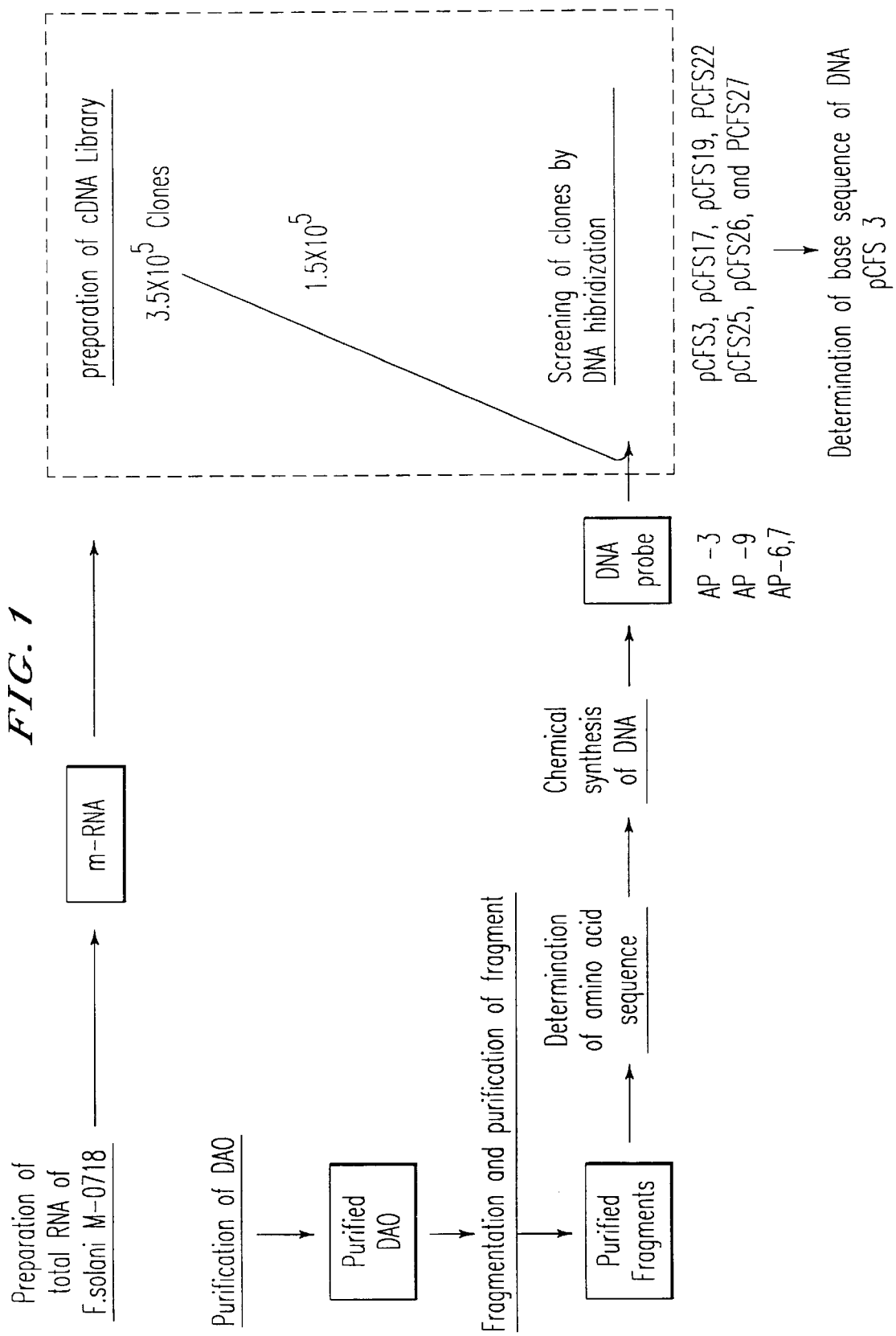
FIG. 1 is a schematic illustration which shows the outline of the process for cloning of the DNA encoding DAO.

The cloning of a DNA encoding DAO of *F. solani* was carried out using conventional procedures in the art. The outline of the process are presented in the accompanying FIG. 1.

cDNA libraries were prepared by disrupting mycelia of *F. solani* M-0718, extracting a total RNA from said disrupted mycelia, and copying mRNA into cDNA.

Figure 2:
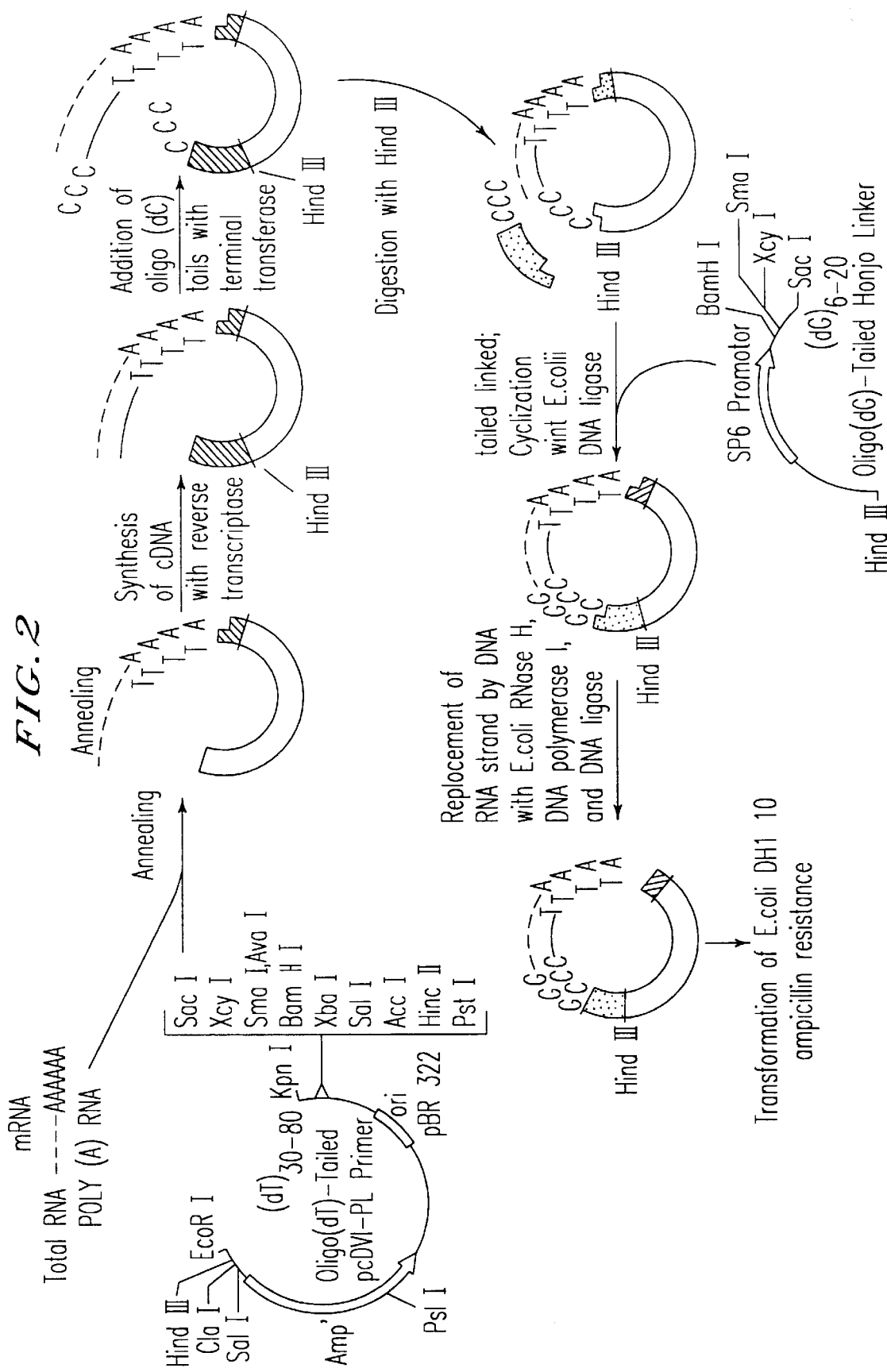
FIG. 2 is a schematic illustration of the preparation protocol for cDNA library.

DNA probes were prepared as follows. Amino acid sequences of several peptide fragments of DAO protein were determined using purified DAO isolated from a cultured broth of *F. solani* M-0718. On the basis of the amino acid sequence of fragments, nine DNA probes were constructed and used to probe cDNA libraries by hybridization. From a positive clone, a DNA was isolated and cloned to obtain plasmid pCFS3 comprising cDNA encoding DAO. The base sequence of the DNA encoding DAO (DAOcDNA) was determined. The schematic illustration of construction protocol for the cDNA library is shown in FIG. 2. The base sequence of DNA encoding DAO and deduced amino acid sequence are shown in FIG. 7.

As the DNA encoding DAO was cloned and its sequence was identified by the invention, one can easily construct expression vectors which enable microorganisms to produce DAO using the known recombinant technology, for example, by inserting the DNA compound into an appropriate site, downstream of a promoter and SD sequence of an expression vector, when a strain of *Escherichia coli* is used as a host cell. This invention can be accomplished using any expression vectors to which the DNA encoding DAO can be inserted, and such vectors are well known to those skilled in the art. For the purpose of the invention, it is preferable to use vectors selected from those functional in *Escherichia coli*. It is also in no way limited to the use of a particular promoter and many promoters can be used, for example, tac, trp, trpIII, and the like. The suitable host cell such as *Escherichia coli* can be transformed with the expression vector comprising the DNA encoding the DAO of this invention in a conventional manner to give the transformant.

Figure 5:
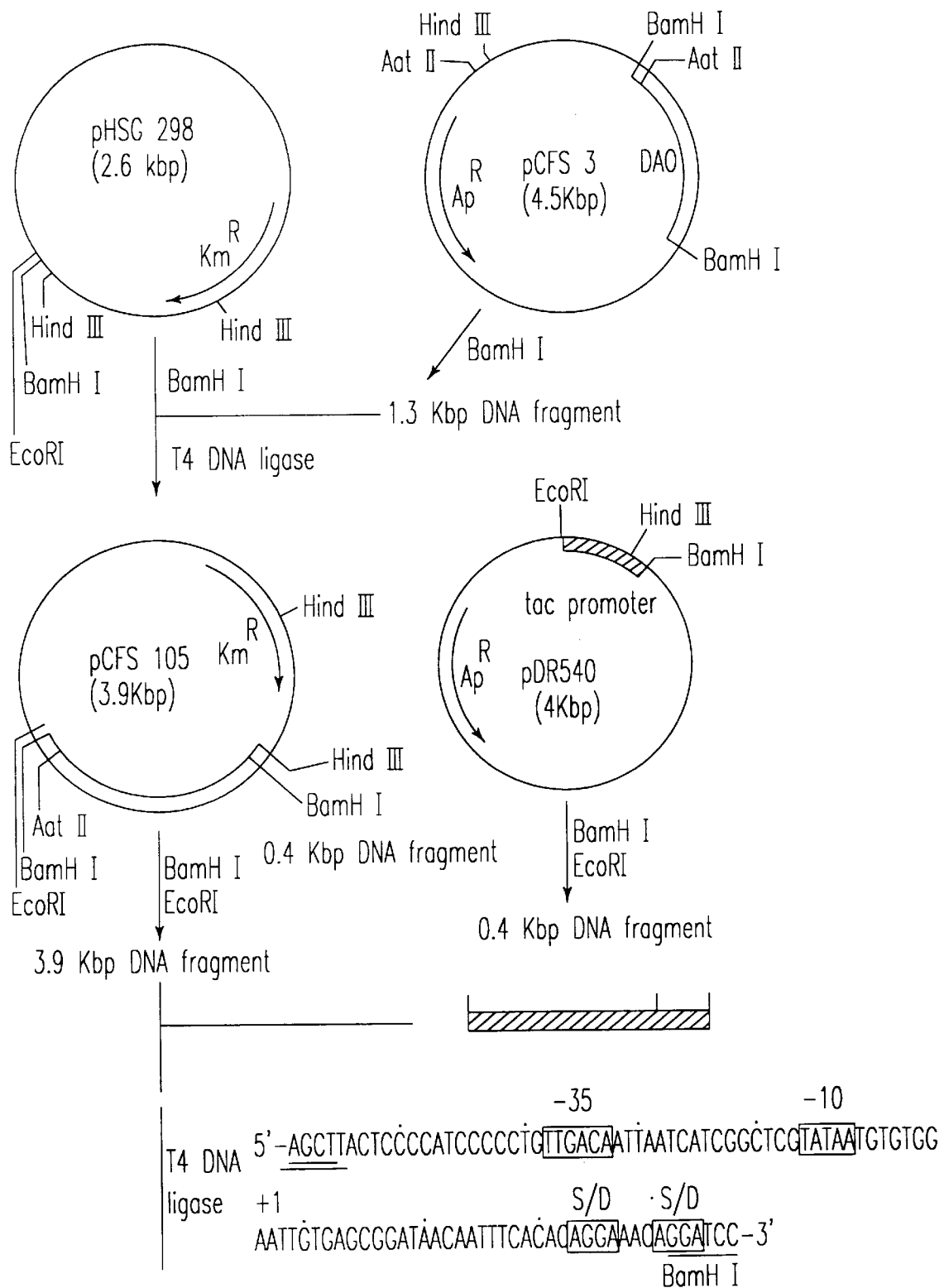
FIG. 5 is a schematic illustration of the construction protocol for plasmid pCF315.
Figure 5:
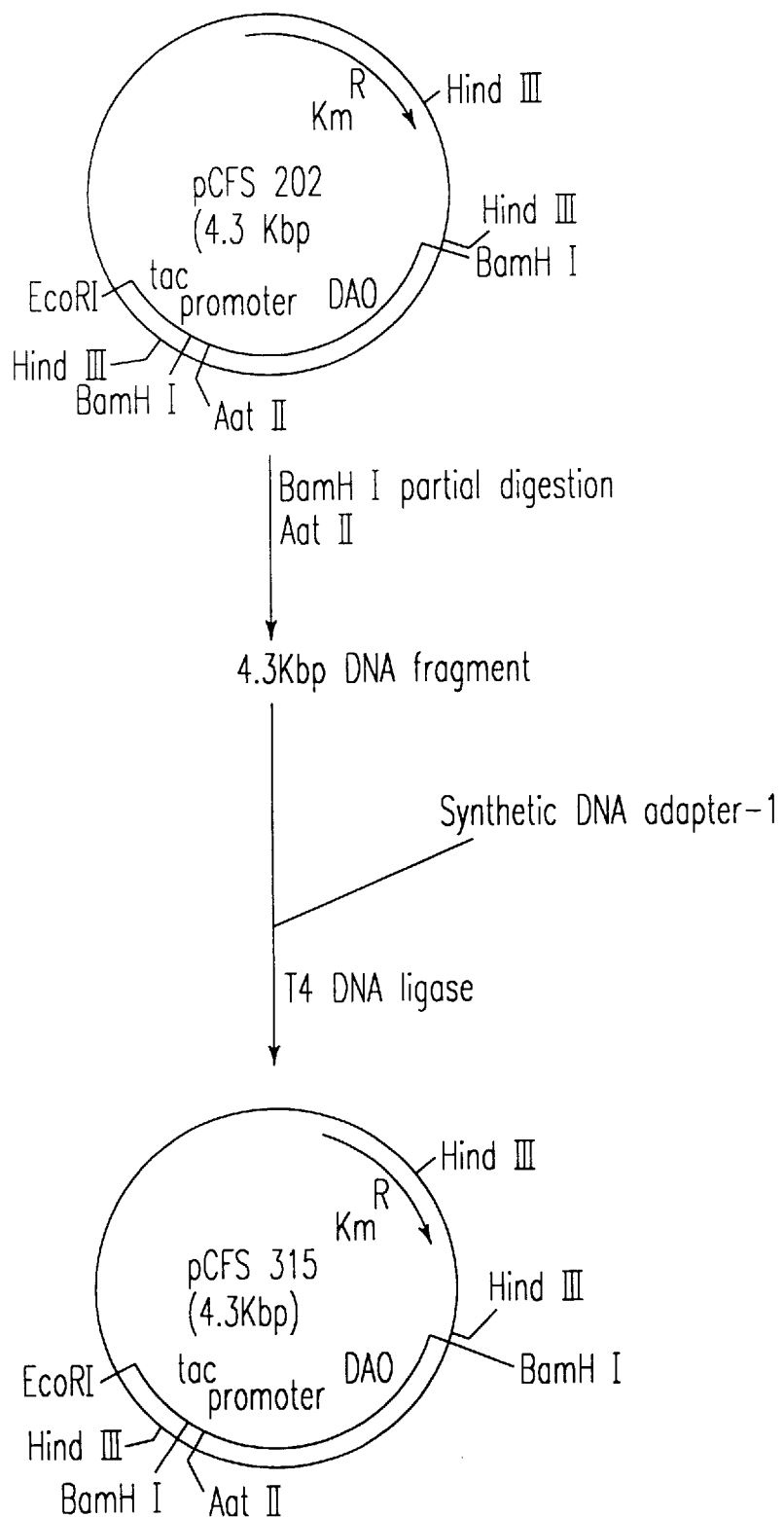

The cultivation of the transformant can be carried out using any of the well known procedures in the art to give the cultured broth. In the working Examples as mentioned below, an illustrative plasmid pCFS315 containing tac promoter, SD sequence and kanamycin resistance-conferring gene was constructed and used to transform *E. coli* JM 109. The resultant transformants expressed products with DAO activities after cultivation. The construction of plasmid pCFS315 is shown in FIG. 5.

Transformants producing DAO activity were harvested and resuspended in a phosphate buffer (PB) and disrupted by sonication. The suspension was then centrifuged to separate the supernatant. The supernatant was dialyzed against PB and the dialyzate was used as the "enzyme preparation". The enzyme preparation reacted on CC to convert into keto-AD-7ACA and GL-7ACA.

Accordingly, this invention further provides a process for the preparation of a compound of the formula (I):

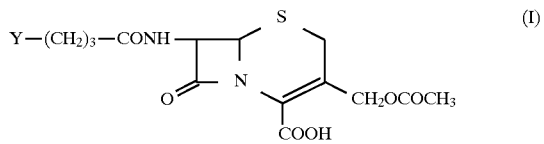

wherein Y is —COCOOH or —COOH or its salts which comprises contacting cephalosporin C or its salt with the cultured broth of the microorganism transformed by DNA encoding DAO of this invention or its processed material.

The processed material of the cultured broth means any preparation which are prepared from the said cultured broth in a conventional manner for elevating the enzyme activity and capable of converting cephalosporin C into the compound (I).

The D-amino acid oxidase activity usually exists in transformed cells. Therefore, the following preparations can be exemplified as a processed material of the cultured broth.

(1) Raw cells; separated from the cultured broth in conventional manners such as filtration and centrifugation (2) dried cells; obtained by drying said raw cells in conventional manners such as lyophilization and vacuum drying (3) cell-free extract; obtained by destroying said raw or dried cells in conventional manners (e.g. autolysis of the cells using an organic solvent, grinding the cells with alumina, sea sand, etc. or treating the cells with super sonic waves)

(4) enzyme solution; obtained by purification or partial purification of said cell-free extracts in conventional manners (e.g. column chromatography)

(5) immobilized cells or enzyme; prepared by immobilizing said cells or enzyme in conventional manners (e.g. a method using acrylamide, glass bead, ion exchange resin, etc.).

The reaction comprising a contact of cephalosporin C with the enzyme can be conducted in an aqueous medium such as water or a buffer solution, that is, it can be usually conducted by dissolving or suspending the cultured broth or its processed material in an aqueous medium such as water or a buffer solution containing cephalosporin C.

Preferable pH of the reaction mixture, concentration of cephalosporin C, reaction time and reaction temperature may vary with properties of a cultured broth or its processed material to be used. Generally, the reaction is carried out at pH 6 to 9, preferably pH 7 to 8, at 5° to 40° C., preferably 5° to 37° C. for 2 to 50 hours.

The concentration of cephalosporin C as a substrate in the reaction mixture may be preferably selected from a range of 1 to 100 mg/ml.

Thus produced compound (I) can be purified and isolated from the reaction mixture in a conventional manner.

To make the invention more efficient and attain the high level production of DAO in $E.$ $coli$, three more expression vectors, plasmids pYS9120A (Amp$^R$), pYS9122K (Km$^R$), and pYS9122C (Cm$^R$) were constructed from pCFS315 by replacing tac promoter with trp promoter and inserting fd phage terminator in the working Examples as mentioned below. These modified vectors were revealed to enable transformed microorganisms to express DAO in higher level. For example, transformants containing plasmid pYS9122K expressed up to 2.5 times more recombinant DAO (r-DAO) than those containing pCFS315. The recombinant DAO (r-DAO) was purified by ammonium sulfate precipitation, hydrophobic column chromatography and DEAE column chromatography. The purified r-DAO had a specific activity of 24.5 units mg protein. The N-terminal amino acid sequence of purified r-DAO was identical with that deduced from cDNA.

This invention provides the purified recombinant DAO with specific activity of more than 10.9 units/mg protein. Once the DNA sequence of DAO is determined, it is easy to obtain active derivatives of DAO by conventional methods, such as site specific change within the scope of the invention. Therefore, this invention also provides active recombinant DAO derivatives.

In the following Examples, some plasmids, enzymes, such as restriction enzymes, T4 DNA ligases, and other materials were obtained from commercial sources and used according to the indication by suppliers. Operations employed for the cloning of DNA, transformation of host cells, cultivation of transformants, recovery of DAO from the cultured broth, and the like are well known in the art or can be adapted from literatures. The literature referred to in the specification are shown by figures and their details are provided at the end part of the specification.

Following examples further illustrate and detail the invention disclosed.

EXAMPLE 1

Cloning of DAO Gene

Cloning of DAO gene was carried out in substantial accordance with the description in the $Molecular$ $Cloning$[1].

A. Extraction and Purification of mRNAs from $F.$ $solani$ M-0718

A.1. Extraction of total mRNA $F.$ $solani$ M-0718 strain were grown in 100 ml of a medium containing 2% glucose, 2% corn steep liquor (CSL), and 0.2% DL-alanine, pH 5.0 at 30° C. for 3 days with shaking. Cells were destroyed under low temperature (−80° C.), and suspended in 40 ml of a guanidine isothiocyanate solution (4M guanidine isothiocyanate, 50 mM Tris-HCl, pH 7.5, 20 mM EDTA, 2% sodium N-lauroylsarcosinate, and 0.17M β-mercaptoethanol) and the resulting mixture was incubated at 60° C. for 5 min. The mixture was then centrifuged at 10,000×g for 10 min and the supernatant was treated with guanidine/cesium chloride ($Molecular$ $Cloning$[1], p.196) to isolate 13 mg of total RNA.

A.2 Purification of Poly (A) RNA with Oligo (dt)-cellulose

Total RNA (3 mg) were purified in accordance with the method of $Molecular$ $Cloning$[1] (p.197) using 200 mg of oligo (dT)-cellulose (Bethesda Research Laboratories; BRL) to obtain 40 μg of Poly (A) RNA (mRNA).

B. Preparation of cDNA Library

The plasmids and enzymes employed are listed below:

Oligo (dT)-tailed pcDV1-PL-primer: Pharmacia, Inc.
Oligo (dT)-tailed Honjo linker: Pharmacia, Inc.
Reverse transcriptase: Seikagaku Kogyo, Inc.
Terminal transferase: Takara Syuzo, Inc.

E. coli DNA ligase: Pharmacia, Inc.
DNA polymerase I: Pharmacia, Inc.
RNase H: Takara Syuzo, Inc.
HindIII: BRL.

The cDNA encoding DAO were prepared in substantial accordance with the method of Okayama and Berg[2].

ss-cDNA (single strand cDNA) was prepared using mRNA (11 µg) obtained in A.2 and 2 µg of oligo (dT)-tailed pcDV1-PL primer in the presence of reverse transcriptase. The ss-cDNA was C-tailed (average 15) with the aid of terminal transferase and cleaved by restriction enzyme HindIII, which was followed by annealing with 0.5 µg of oligo (dT)-tailed Honjo linker. The annealing mixture was treated with E. coli DNA ligase, and then RNase H, DNA polymerase I, and E. coli ligase. The resultant ds-cDNA (double stranded cDNA) was used to transform E. coli DH1 (ATCC 33849) in substantial accordance with the procedure of Hanahn[3]. From transformants, 3.5×10$^5$ of Am$^R$ clones were isolated. The schematic illustration of preparation protocol for the cDNA library is shown in FIG. 2.

C. Purification of DAO and Preparation of DNA Probes

Purification of DAO was carried out using a conventional method for the isolation and purification of enzymes from microorganisms.

C.1. Cultivation of F. solani M-0718

F. solani M-0718 strain was grown in a 500 ml of Erlenmyer flask containing 100 ml of a culture medium comprising 2% glucose, 2% CSL, 0.5% DL-alanine, pH 5.0 at 30° C. for 3 days with shaking. A portion (5 ml) of the culture was transferred into 100 ml of the fresh medium and the cultivation was continued for additional 30 hours at 30° C.

C.2. Extraction and Purification of DAO

Figure 3:
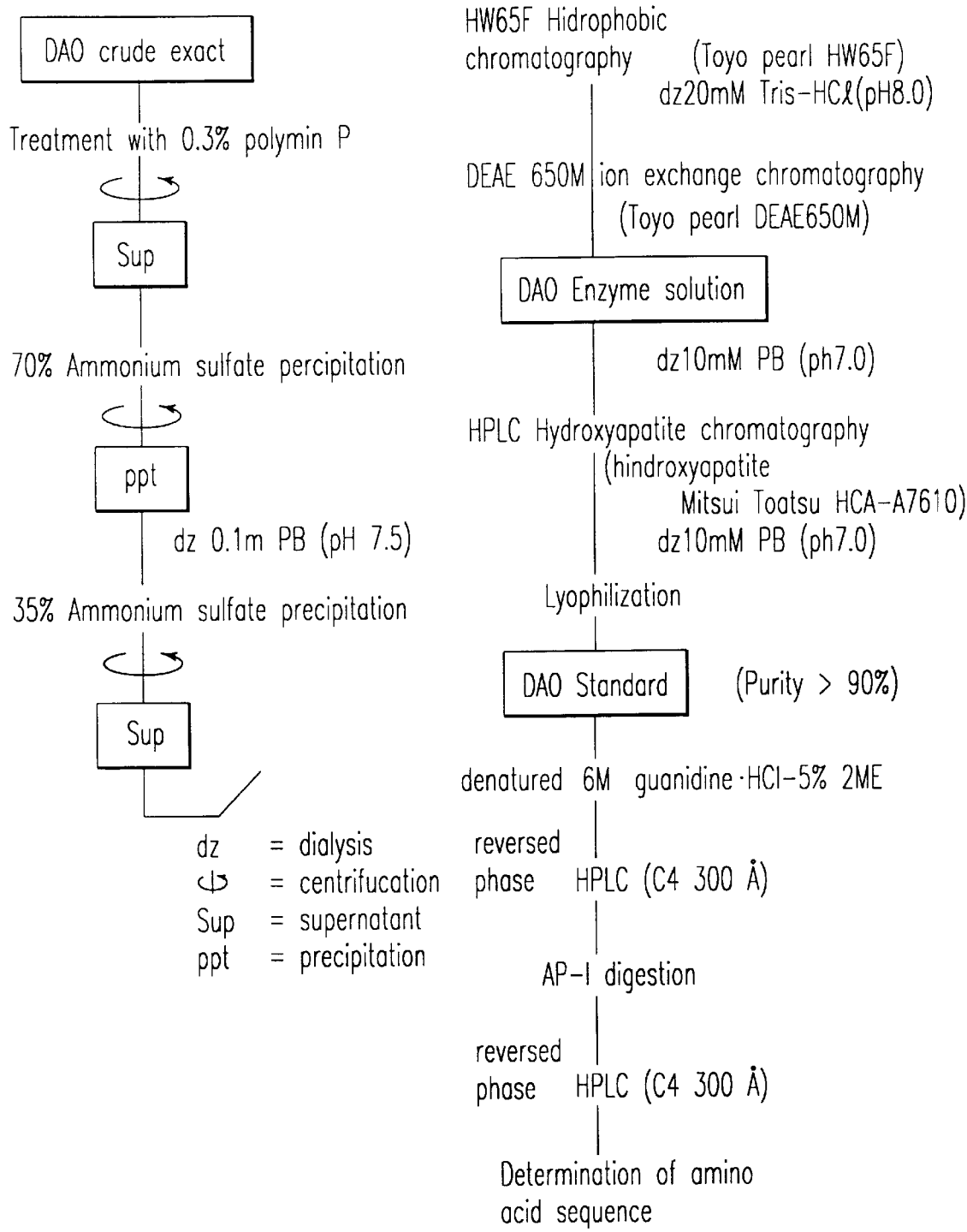
FIG. 3 is a flow chart which shows the process of the purification of DAO and determination of a partial sequence of amino acids.

Purification of DAO from the cultured broth obtained in C.1. was carried out according to the protocol shown in the flow chart in accompanying FIG. 3.

A slurry (500 ml) of the cells was prepared by centrifuging (6,000×g, 5° C., 10 min) the cultured broth obtained in C.1., followed by washing with 0.1M phosphate buffer (PB). The slurry was mixed with an equal volume (500 ml) of sea-sand and ground thoroughly in a mortar. The resulting paste was diluted by about 500 ml of PB and filtered with suction. The filtrate was recovered as a crude DAO extract.

After the removal of nucleic acids by treating with 0.3% polyethyleneimine, the crude DAO was subjected to the 70% ammonium sulfate precipitation and centrifugation (6,000 rpm×10 min). The cell pellet was resuspended in 0.1M phosphate buffer (PB), pH 7.5. The suspension was dialysed overnight against 0.1M PB, pH 7.5 and the resultant solution was subjected to the 35% ammonium sulfate precipitation and centrifugation (6,000 rpm×10 min) to recover 110 ml of supernatant. The supernatant was then applied to a hydrophobic chromatography (column; Toyopearl HM65F®, Toyo Soda Kogyo, volume; 200 ml, size; ×26 mm, wash; 0.1M PB, pH 7.5 with 35% ammonium sulfate (500 ml), eluent; 0–35% ammonium sulfate in 0.1M PB, pH 7.5, linear gradient) and peaks having activity were collected. The fractions were then combined (150 ml) and dialyzed overnight against 20 mM Tris-HCl, pH 8.0. The resultant dialyzate (160 ml) was subjected to the ion exchange chromatography (column; Toyopearl DEAE®, Toyo Soda Kogyo, volume; 120 ml, size; ×26 mm, wash; 20 mM Tris-HCl, pH 8.0 (250 ml), eluent; 20 mM Tris-HCl, pH8.0, 20 mM Tris-HCl, pH 8.0 with 0.3M NaCl, linear gradient (600 ml)) and peaks having activity were collected (90 ml) and dialyzed against 10 mM PB, pH 7.0. A portion (22 ml) of the dialyzed solution was chromatographed on hydroxyapatite column (hydroxyapatite HCA-A7610®, Mitsui Toatsu Kagaku, size; 7.6×100 mm, mobile phase; 10 mM PB. pH 7.0→300 mM PB, pH 7.0, linear gradient over 30 min, flow rate; 1 ml/min, detection; UV at 280 nm) and peaks having activity were collected (5 ml). The rest of the dialyzate (22 ml) was chromatographed in the same manner using hydroxyapatite column and 5 ml fractions with activity were collected. The fractions with activity were combined and lyophilized to yield about 10 mg of DAO powder of more than 90% in purity. The purified preparation gave a single band on SDS-PAGE. A comparison with standard proteins showed that the DAO has a molecular weight of 40,000±1,000 dalton on SDS-PAGE.

C.3. Determination of Partial Amino Acid Sequences

DAO was denatured as follows. Lyophilized DAO (850 µg, prepared in C.2.) was dissolved in a mixture of 6M guanidine.HCl and 5% 2-mercaptoethanol and incubated at 37° C. for 4 hours. The reaction mixture was subjected to the reversed phase HPLC (column; Cosmosil 5C$_4$-300 (Nakarai Tesk, Inc.), flow rate; 1 ml/min, eluent; 0.05% TFA→0.05% TFA/60% CH$_3$CN gradient over 30 min, detection; UV at 220 nm) and the fractions of main peak were pooled.

Figure 4:
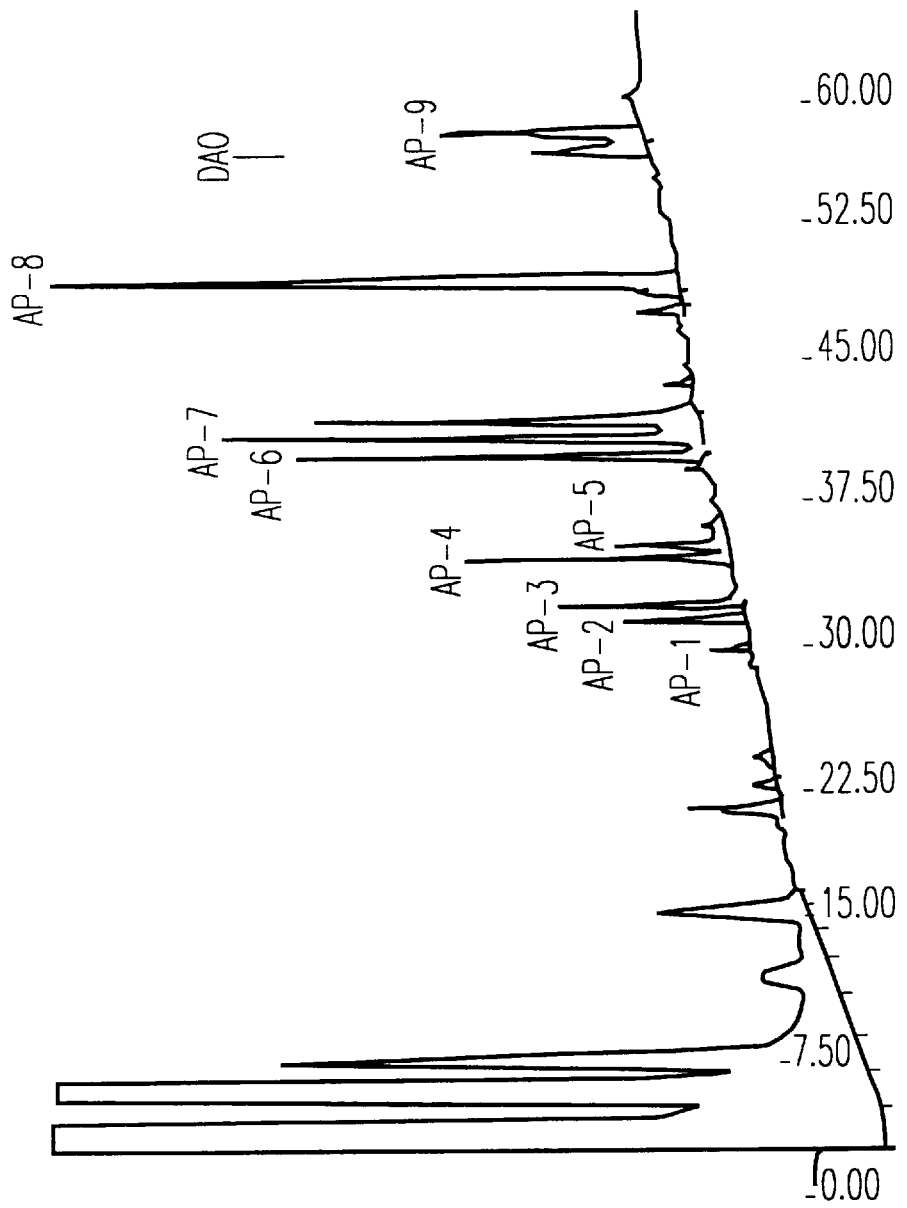
FIG. 4 shows the elution patterns of peptide fragments, AP-1 to AP-9 from the reversed phase HPLC.

The denatured DAO (400 µg) was dissolved in 0.8 ml of 50 mM Tris-HCl buffer and to the solution was added Achromobacter Protease I (AP-I, lysil-endopeptidase) (S/E= 500). After 2 hours incubation at 37° C., the mixture was centrifuged to discard insoluble substances. To the supernatant was added 5% mercaptoethanol and the mixture was subjected to the reversed phase HPLC (r-HPLC) in the same manner as described above except for that the elution was continued for 60 min. The peaks containing fragments AP-1~AP-9 were pooled, respectively. The elution patterns of r-HPLC are shown in FIG. 4.

The amino acid sequence of each peptide fragment was determined in accordance with the method described in "Methods in Enzymology, vol. 91[4)5)]" using 470A gas-phase protein sequencer (Applied Biosystems, Inc.). These nine peptide fragments consist of 98 amino acids were identified as shown below.

```
AP-1(SEQ ID NO: 6):  Arg—Ala—Ile—Leu—Asn—Asp—Ile—Ser—Glu—Ala—Lys
AP-2(SEQ ID NO: 7):  Glu—Pro—X—Phe—Lys
AP-3(SEQ ID NO: 8):  Arg—Leu—Val—Glu—Glu—Val—Pro—Glu—Ala—Gly—Val—His—Phe—Gln—Lys
AP-4(SEQ ID NO: 9):  Gly—Leu—Ser—Val—Ile—Arg—X—Ala—Val—Gly—Met
AP-5(SEQ ID NO: 10): Thr—Pro—Asn—Ile—Ile—Val—Asn—Ala—Thr—Gly—Leu—Gly—Ser—Tyr—Lys
AP-6(SEQ ID NO: 11): His—Met—Pro—Gly—Asp—Tyr—Asp—Val—Glu—Tyr—Ala—Ser
AP-7(SEQ ID NO: 12): His—Met—Pro—Gly—Asp—Tyr—Asp—Val—Glu—Tyr—Ala—Ser—X—Phe—Ala
AP-8(SEQ ID NO: 13): Thr—Met—Ala—Pro—Ala—Arg—Gly—Gln—Ile—Val—Val—Val—
                     Arg—Asn—Glu—Ser—Ser—Pro—Met—Leu—Leu
AP-9(SEQ ID NO: 14): Asn—Met—Phe—Glu—Asp—Phe—X—Glu—Gln
X: undetermined
```

These amino acid sequences are consistent with the corresponding regions of the deduced amino acid sequence from the cDNA prepared in Example 1 (see, FIG. 8).

D. Preparation of DNA Probes

A mixture of oligonucleotides (DNA probe) was prepared from AP-3, AP-9 and AP-6, 7 in order to probe the cDNA library prepared above B.

DNA probe AP-3 was prepared by synthesizing oligonucleotides on the basis of the amino acid sequence of peptide fragment AP-3 shown above by including as many potential DNA sequences encoding said AP-3 as possible so that any of synthesized oligonucleotides might hybridize with the corresponding region (same as AP-3) on the DAO gene. Two more DNA probes AP-9, and AP-6, 7 were constructed in the same manner on the basis of peptide fragments AP-9 and AP-6, 7, respectively. Oligonucleotides were synthesized with a commercially available Model 381-A DNA Synthesizer (Applied Biosystems, Inc.). Deducation of the DNA sequence encoding a given amino acid sequence was performed by the use of codons found in high frequency in *F. solani*, referring to the codon usage of Cutinase of *Fusarium solani* (Soliday[6]).

Following DNA probes were synthesized in this manner.

DNA Probe AP-3 (a mixture of 16 kinds of 36 mers)

GAG GAG GT$^T_C$ CCT GAG GC$^T_C$ GG$^T_C$ GT$^T_C$ CAC TTC CAG AAG (SEQ ID NO: 15)

Glu Glu Val Pro Glu Ala Gly Val His Phe Gln Lys (SEQ ID NO: 16)

DNA Probe AP-9 (a mixture of 4 kinds of 18 mer)

AA$^T_C$ ATG TTC GAG TTC (SEQ ID NO: 17)

Asn Met Phe Glu Asp Phe (SEQ ID NO: 18)

DNA Probe AP-6 and AP-7 (AP-6, 7) (a mixture of 16 kinds of 26 mer)

ATG CCT GG$^T_C$ GA$^T_C$ TAC GA$^T_C$ GC$^T_C$ GAG TA   SEQ ID NO: 19)

Met Pro Gly Asp Tyr Asp Val Glu Tyr (SEQ ID NO: 20)

E. Selection and Separation of DAO Clone from cDNA Library

E.1. Labelling of DNA Probe

DNA probes, AP-3, AP-9, and AP-6, 7 prepared in above D were labelled with γ-$^{32}$P-ATP in the presence of T4 polynucleotide kinase according to the method of Inglia[7].

E.2. Screening by $^{32}$P-labelled AP-3 Probe

*E. coli* DH1 cells containing 1.5×10$^5$ of cDNA libraries (prepared in B.2.) were grown on a L-broth-agar plate containing 50 μg/ml of ampicillin at 37° C. for 10 hours until colonies appeared. The colonies were transferred onto nitrocellulose filter and incubated 12 hours in the same medium containing 250 μg/ml of chloramphenicol. After cells were lysed and denatured with 0.5N NaOH–1.5N NaCl, the mixture was neutralized with 0.5N Tris-HCl, pH 7.0–1.5N NaCl and subjected to the hybridization with DNA probe AP-3 in accordance with the teaching of Davis[8].

The filter was incubated at 37° C. in a mixture of about 3×10$^6$ cpm/ml of AP-3, 50% (v/v) formamide, 5×SSPE (0.9M NaCl, 50 mM NaHPO$_4$, 5 mM EDTA, pH 7.0), 1×BFP [0.02% bovine serum albumin, 0.02% Ficol (m.w. 400,000), 0.02% polyvinylpirolidone], 0.3% SDS (sodium dodecyl sulfate), and 100 μg/ml of sonicated denature-carrier DNA (bovine thymus). After an overnight incubation at 37° C., the filter was washed in 20 mM phosphate buffer (PB), 0.2% SDS and 1 mM EDTA successively at 37° C. (×3), dried and visualized by autoradiography (exposure: −80° C. for 3 days). Many colonies were positive for hybrydization. Thirteen clones were picked from the positive colonies and grown in a liquid medium. Plasmid DNA was prepared from the cultured clone in accordance with the method of Davis[9] and electrophoresed on agarose-gel. The resultant plasmid DNAs were then tested by southern hybridization (Southern [10]) using DNA probes AP-3, AP-9 or AP-6, 7 as probes. The hybridization was carried out under the same conditions as described above with some exceptions. That is, in case DNA probes AP-9 and AP-6, 7 are used, the hybridization was conducted in a mixture of 6×SSC (0.9M NaCl, 0.09M sodium citrate, pH 7.0), 5×BFP, 0.5% SDS, 100 μg/ml of carrier DNA and labelled DNA probes under the temperature of 37° C. (AP-6), 45° C. (AP-9) or 50° C. (AP-6, 7). Each overnight culture was washed with 6×SSC at 37° C. (AP-9) or 50° C. (AP-6, 7) (1×), and then at 37° C. (2×). The reaction conditions are listed in the Table 1.

TABLE 1

Conditions used for the Hybridization with Synthetic Probes

|  | conditions hybridization | conditions wash |
| --- | --- | --- |
| Ap-3 | 50% formamide 5 × SSPE, 37° C., 15 hr | 20 mM PB with 0.2% SDS 37° C. |
| AP-9 | 6 × SSC 37° C., 15 hr | 6 × SSC 37° C. |
| AP-6, 7 | 6 × SSC 45° C., 15 hr | 6 × SSC 50° C. |

All filters were visuallized by the autoradiography (−80° C., overnight) and seven positive clones were selected and designated; pCFS3, pCFS17, pCFS19, pCFS22, pCFS25, pCFS26 and pCFS27. Seven plasmid DNAs were individually cleaved with restriction enzyme BamHI and the resulting fragments were tested again by southern hybridization [10] using labelled DNA probes AP-3, AP-9 or AP-6, 7 as DNA probes. All probes hybridized with ~1.3 kb and ~1.1 kb DNA fragments. One of plasmids containing ~1.3 kb fragment were named pCFS3.

F. Sequencing and Identification of DAO Clone

Plasmid pCFS3 were digested with restriction enzyme BamHI to isolate ~1.3 kb BamHI restriction fragment. The base sequence of said ~1.3 kb fragment was determined by dideoxy chain termination method of Sanger [12] using vectors M13mp10 and M13mp11[11], α-$^{32}$P-dATP with a commercially available instrument, Sequenase® (United States Biochemical Corporations, imported and marketed by Toyobo). A restriction site and function map of plasmid pCFS3 is presented in FIG. 5 of the accompanying drawings and the base sequence of 11.3 kb BamHI restriction fragment of plasmid pCFS3 is presented in FIG. 6. FIG. 6 shows that the 11.3 kb BamHI fragment contains regions consistent with fragments AP-6, 7, AP-3, and AP-9 between nucleotides 171–196, 294–329 and 420–437, respectively. In FIG. 6, the nucleotide 1280 (symbol X) is not identified.

FIG. 7 shows that the amino acid sequence deducated from pCFS3 DNA contains a 1086 bp open reading frame (ORF). FIG. 8 shows that said ORF contains partial amino acid seqeunces which are consistent with those of 9 peptide fragments derived from DAO protein (AP-1 to AP-9, Example 1 A., A.3). These evidences lead us to a conclusion that the clone plasmid pCFS3 is identical with DAO gene and have a complete ORF.

Thus, the DAO of this invention has a peptide sequence as shown in FIG. 7 which contains the following characteristic peptide fragments:

AP-1(SEQ ID NO: 6): Arg—Ala—Ile—Leu—Asn—Asp—Ile—Ser—Glu—Ala—Lys
AP-2(SEQ ID NO: 21): Glu—Pro—Trp—Phe—Lys
AP-3(SEQ ID NO: 8): Arg—Leu—Val—Glu—Glu—Val—Pro—Glu—Ala—Gly—Val—His—Phe—Gln—Lys
AP-4(SEQ ID NO: 22): Gly—Leu—Ser—Val—Ile—Arg—His—Ala—Val—Gly—Met
AP-5(SEQ ID NO: 10): Thr—Pro—Asn—Ile—Ile—Val—Asn—Ala—Thr—Gly—Leu—Gly—Ser—Tyr—Lys
AP-7(SEQ ID NO: 23): His—Met—Pro—Gly—Asp—Tyr—Asp—Val—Glu—Tyr—Ala—Ser—Pro—Phe—Ala
AP-8(SEQ ID NO: 13): Thr—Met—Ala—Pro—Ala—Arg—Gly—Gln—Ile—Val—Val—Val—
Arg—Asn—Glu—Ser—Ser—Pro—Met—Leu—Leu
AP-9(SEQ ID NO: 24): Asn—Met—Phe—Glu—Asp—Phe—Arg—Glu—Gln
The AP-6 is included in the AP-7.

EXAMPLE 2
Construction of Expression Vector pCFS315 Encoding DAO Gene

A. Construction of Km$^R$ Plasmid pCFS105 Encoding DAO

BamHI restriction fragments of o.5 μg of plasmid pHSG298 (Km$^R$ pUC type vector, Takara Syuzo) and 2 μg of plasmid pCFS3 were ligated in the presence of 2 units of T4 DNA ligase. The ligation mixture was used to transform E. coli JM 109 (Takara Shyzo) according to the method described in the literature (Hanahan[3]) in a ligation buffer. The mixture was then placed on L-broth agar containing 20 μg/ml kanamycin, 2 mM IPTG (isopropyl-β-D-thigalactopyranoside), and 0.5 mg/ml X-Gal (5-bromo-4-chloro-3-indolyl-β-galactoside). Plasmid DNAs were extracted from white colonies grown, from which was selected the plasmid pCFS105 having lac promoter from pHSG298 in the same direction as DAO gene.

B. Construction of Plasmid DCFS202 Containing tac Promoter

Expression vector pDR540 (Pharmacia, Inc.) containing tac promoter was digested with EcoRI and BamHI to isolate 0.4 kb EcoRI-BamHI restriction fragment which encodes tac promoter and SD sequence required for the translation. A partial base sequence (SEQ ID NO: 25) of the 0.4 kb EcoRI-BamHI fragment is shown in FIG. 5.

Plasmid pCFS105 prepared in the above A. was digested with BamHI (partial) and EcoRI to isolate 3.9 kb DNA fragment, which was ligated to the 0.4 kb DNA fragment in the presence of T4 DNA ligase. The ligation mixture was used to transform E. coli JM 109[3]. Blue colored colonies were isolated in the same manner as A. In this case, the consistency between the DNA sequence corresponding to the pCDV1-PL primer present in the region of downstream from polyA sequence of cDNA of DAO and the frame for the translation of N-terminal seequence of β-galactosidase gene from pHSG298 allows the read through of tac promoter and induce the generation of β-galactosidase, which results in the blue colored colonies. Plasmid DNA was isolated from a strain in a blue colony and the structure of pCFS202 was confirmed by restriction enzyme analysis.

C. Preparation of Synthetic DNA Adapter I

Plasmid pCFS202 contains too many nucleotides (62 bp) between the SD sequence for the tac promoter and the ATG translational initiation codon to enable E. coli host cells to express a recombinant DNA compound of the invention. A synthetic adapter I was constructed to decrease the number of these nucleotides by seven using two oligonucleotides, as follows.

58mer (SEQ ID NO: 26) 5'GATCCAATCATGTC CAACACAATC GTCGTCGTTG
50mer (SEQ ID NO: 27)      3'GTTAGTACAG GTTGTGTTAG CAGCAGCAAC
                           GTGCCGGTGT CATTGGCTTG ACGT-3'
                           CACGGCCACA GTAACCGAAC-5'

Two oligonucleotides were synthesized with 381-A DNA Synthesizer (Applied Biosystems) separately and added to a reaction buffer at the concentration of 100 μg/ml each and the mixture was incubated at 95° C. for 5 min. The annealing was completed by cooling the mixture to the room temperature gradually.

D. Construction of Expression Plasmid DCFS315

Plasmid pCFS202 was partially digested with BamHI. The partially digested pCFS202 was then cleaved with AatIII to isolate 4.3 kb DNA fragment. The 4.3 kb fragment (0.5 μg) was ligated to the annealed synthetic adapter I in the presence of T4 DNA ligase and the ligation mixture was used to transform E. coli JM 109. Transformants were selected on a L-Broth agar plate containing 20 μg/ml kanamycin. Desired plasmid pCFS315 was isolated from one of growing cells and characterized by restriction enzyme mapping. The DNA sequence in the region corresponding to the adapter was confirmed by dideoxy chain termination method[13]. The schematic illustration of the construction protocol for plasmid pCFS315 is presented in FIG. 5. FIG. 5 shows also the construction protocol for intermediate plasmids pCFS105 and pCFS202.

EXAMPLE 3

Growth of Transformant *E. coli* JM 109/pCFS315 and Assay of Expressed DAO

A. Growth of Transformants and Preparation of Enzyme Preparation

The cells of *E. coli* JM 109/pCFS315 (constructed in Example 2) were innoculated to 200 ml of L-broth containing 20 μg/ml kanamycin and 1 mM IPTG and incubated at 37° C. for 24 hours with shaking. Cells were harvested by centrifugation at 6,000×g for 10 min at 5° C., and resuspended in 10 ml of 20 mM PB (pH 7.5), which was followed by sonication. After centrifuging the suspension, the supernatant was isolated and dialyzed against 3 ml of PB. The dialyzed solution (dialyzate) was used as the "enzyme preparation" of DAO.

A 1.0 mg/ml solution of previously prepared lyophilized DAO (purity>90%, Example 1, C., C.2.) (the concentration was determined by the Lowry method using bovine serum albumin as the standard) was used as the reference, "enzyme standard" in the following assay involving enzymatic reactions using CC as substrate.

B. Assay of the Enzyme Preparation

In a total volume of 1 ml of a reaction mixture, 10.8 mM CC, 100 mM PB (pH 7.5) and 50 μl of the enzyme preparation were reacted at 30° C. for 120 min. The resultant mixture containing the enzyme reaction products was assayed by HPLC (column; Inertsil ODS-2, Gas-chlo industry, eluate; 6.6 mM PB, pH 7.0 with 3% methanol, detection; 254 nm). As a result, 4.75 mM keto-AD-7ACA, 6.28 mM GL-ACA and no CC were detected.

C. The Specific Activity of Enzyme Preparation

The enzyme preparation and the 1.0 mg/ml enzyme standard prepared above A. and B. were used to determine the specific activity (enzyme activity per protein).

The enzyme preparation (12.5 μl) was reacted in 1 ml of a reaction mixture in the same manner as described in B. The reaction mixture was analyzed with HPLC and the amount of CC, keto-AD-7ACA and GL-7ACA were determined. The protein concentration of the enzyme preparation was determined with Protein Assay Kit (Biorad, Inc.) using the 1.0 mg/ml DAO enzyme standard as the standard. The specific activity of the enzyme preparation was calculated from the decrease in CC and the sum of the increases in (or formation of) keto-AD-7ACA and GL-7ACA.

The specific activity of the 1.0 mg/ml DAO enzyme standard (10 μl) was determined in the same manner except for that the enzymatic reaction was continued only for 60 min.

When the specific activity of the DAO standard was assumed to be 100%, that of the enzyme preparation was 7.8% based on the decrease of CC or the production of keto-AD-7ACA and GL-7ACA.

The *Escherichia coli* JM109/pCFS315 was deposited in the Fermentation Research Institute, Agency of Industrial Science and Technology, 1–3, Higashi 1 chome, Tsukuba-shi, Ibaraki-ken, Japan, with the accetion number of FERM BP-1916 on Jun. 20, 1988 according to the stipulations of the Budapest Treaty.

EXAMPLE 4

Construction of Plasmid p322A/C pBR322 (10 μg) was digested with AatII (10 units, Toyobo) and ClaI (Boehringer Manheim) in 100 μl of a buffer [10 mM Tris-HCl (pH 7.5), 7 mM MgCl$_2$, 60 mM KCl, 7 mM 2-mercaptoethanol, 100 μg/ml BSA] and the approximately 4.3 kb DNA (restriction fragment) was isolated by 0.8% agarose gel electrophoresis.

Figure 11:
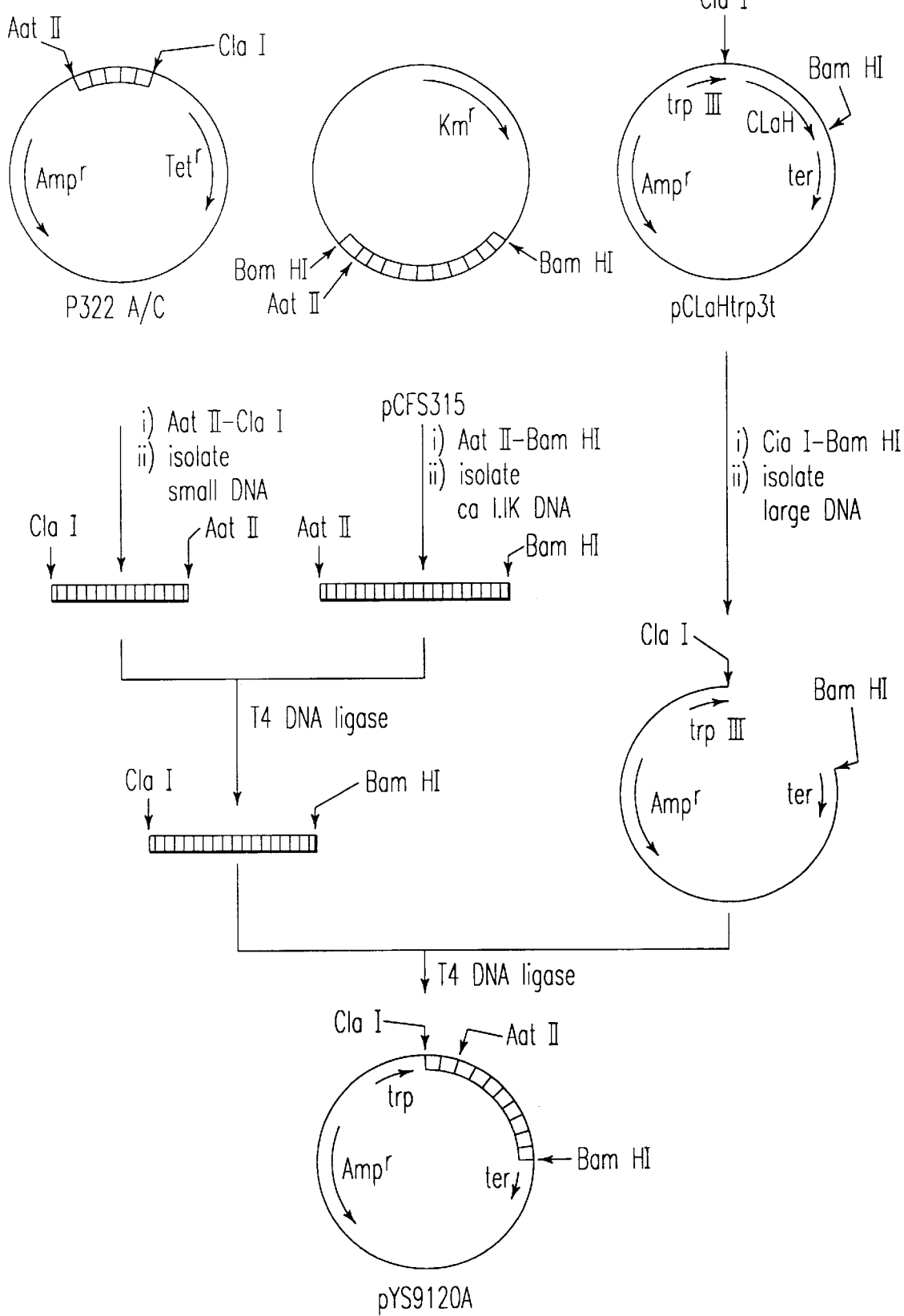
FIG. 11 is a schematic illustration of the construction protocol for the plasmid pYS9120A.

DNA oligomers DAO-1 (56mer (SEQ ID NO: 28)) and DAO-2 (50mer SEQ ID NO: 29)) were synthesized with a DNA synthesizer 381A (Applied Biosystems). These oligomers were designed to give an annealing duplex with single-stranded DNA ends characteristic of ClaI and AatII restriction enzyme cleavage so that it can be ligated to ClaI site of trp promoter (ClaI type) and AatII site of DAO DNA (see, FIG. 11).

Figure 10:
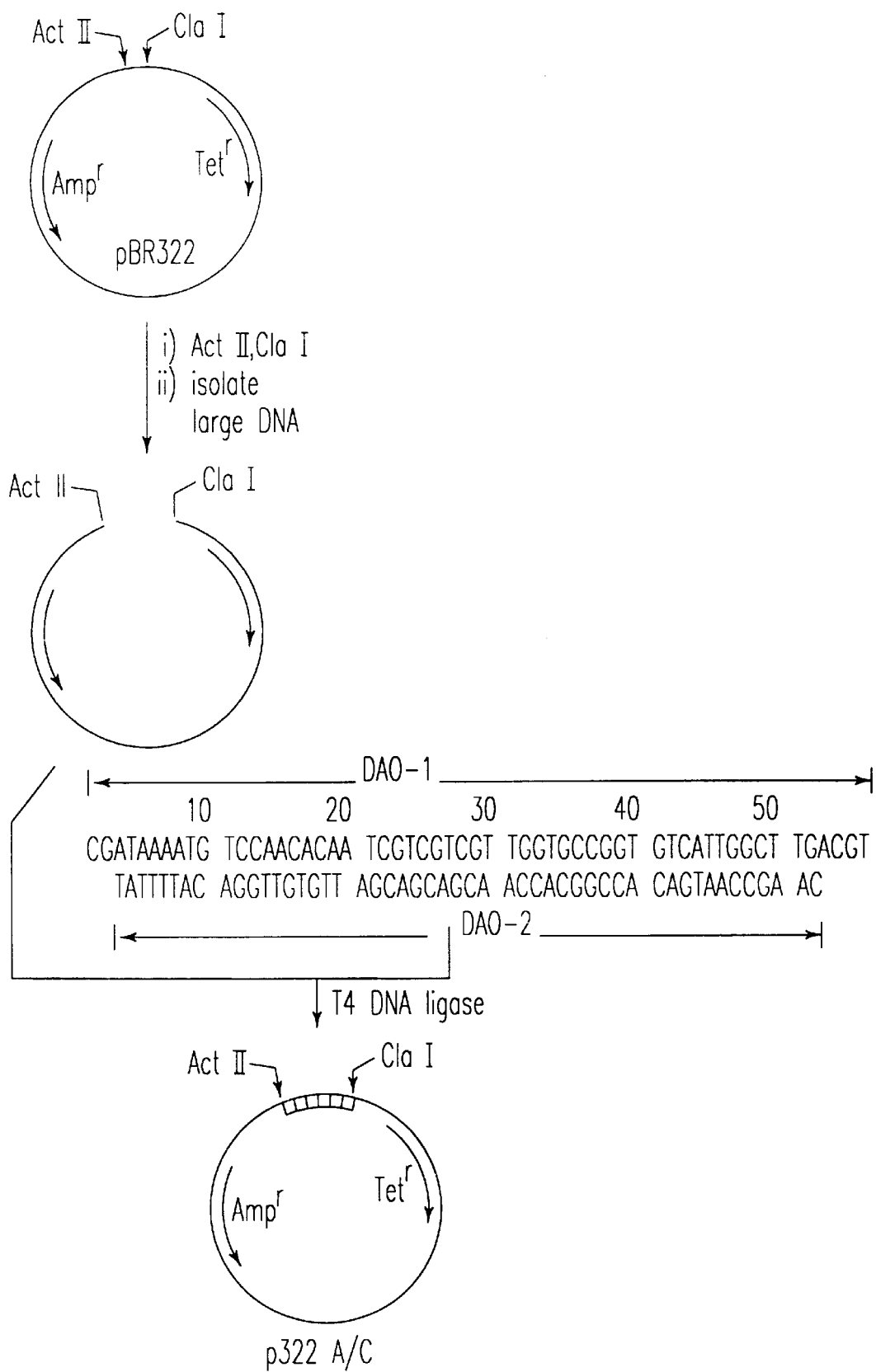
FIG. 10 is a schematic illustration of the construction protocol for the plasmid p322A/C.

The approximately 4.3 kb DNA fragment (200 ng), DAO-1 (9.7 pmole) and DAO-2 (38.5 pmole) was reacted in 20 μl of a reaction buffer [50 mM Tris-HCl (pH 7.8), 10 mM MgCl$_2$, 20 mM dithiothreitol (DTT), 1 mM ATP, 50 μg/ml BSA] in the presence of T4 DNA ligase (300 units, Takara Shuzo) at 15° C. for 60 min. The ligation mixture was used to transform *E. coli* JM 109 according to the method described in the literature [Shigesada, K. (1983), Saibo Kogaku, 2, 616–626]. From one of the transformants, the desired plasmid p322A/C was isolated and characterized by restriction enzyme mapping. The schematic illustration of the construction protocol for plasmid p322A/C is presented in FIG. 10.

EXAMPLE 5

Construction of Plasmid pYS9120A p322A/C (10 μg) was digested with AatII (10 units) and ClaI (10 units) and approximately 54 bp DNA fragment was isolated by 2.25% agarose gel electrophoresis. pCFS315 constructed in Example 2 (10 μg) was digested with AatII (10 units) and BamHI (10 units) and approximately 1.1 kb DNA fragment was isolated by 0.8% agarose gel electrophoresis. pCLaHtrp3t (European Patent Publication No. 0206769) (10 μg) was digested with ClaI (10 units) and BamHI (10 units) to isolate the approximately 3.8 kb restriction fragment.

The 54 bp ClaI-AatII restriction fragment (50 ng), the 1.1 bp AatII-BamHI restriction fragment (50 ng) and the 3.8 bp ClaI-BamHI restriction fragment (200 ng) were ligated in the presence of T4 DNA ligase (300 units) in a similar manner as described in Example 4. *E. coli* JM109 was transformed by the ligation mixture, and the desired plasmid pYS9120A was isolated from one of the transformants by extraction. The schematic illustrations of the construction protocol for plasmid pYS920A is presented in FIG. 11.

EXAMPLE 6

Construction of Plasmid p153trp

A new trp promoter (trp V) with EcoRI and ClaI ends was prepared in the following manners.

A 104 bp DNA fragment was constructed using synthetic oligomers which were divided into groups I (A'), II (B', C, D, E, F, G), III (G, H, I, J), IV (K, L, M') and V (N'). Each oligomers in group II (0.2 nmole, respectively) was phosphorylated with T4 polynucleotide Kinase (2.5 units, Takara Shuzo) in 100 μl of a ligation buffer (described in Example 1) at 37° C. for 60 min. The reaction mixture was heated at 65° C. for 20 min to inactivate the enzyme. The resulting mixture was then incubated at 15° C. for 30 min in the presence of T4 DNA ligase (600 units) and 20 mM ATP (5 μl). The oligomers in group II and III were phosphorylated and ligated in the similar manner as described above. The ligation mixtures prepared from group II, III, and IV were mixed and the mixture was incubated at 15° C. for 30 min after the addition of T4 DNA ligase (600 units) and 20 mM ATP (5 µl). Finally, oligomers A' and N' (0.4 nmole, respectively), T4 DNA ligase (600 units) and 20 mM ATP (5 µl) were added to the mixture, and the resultant mixture was incubated at 15° C. for 30 min. The desired approximately 104 bp restriction fragment was isolated from the ligation mixture by 2.25% agarose gel-electrophoresis.

pAT153 (10 µg, Pharmacia) was digested with EcoRI (10 units, Toyobo) and ClaI (10 units) and the approximately 3.6 kb restriction fragment was isolated by 0.8% agarose gel electrophoresis.

Figure 12:
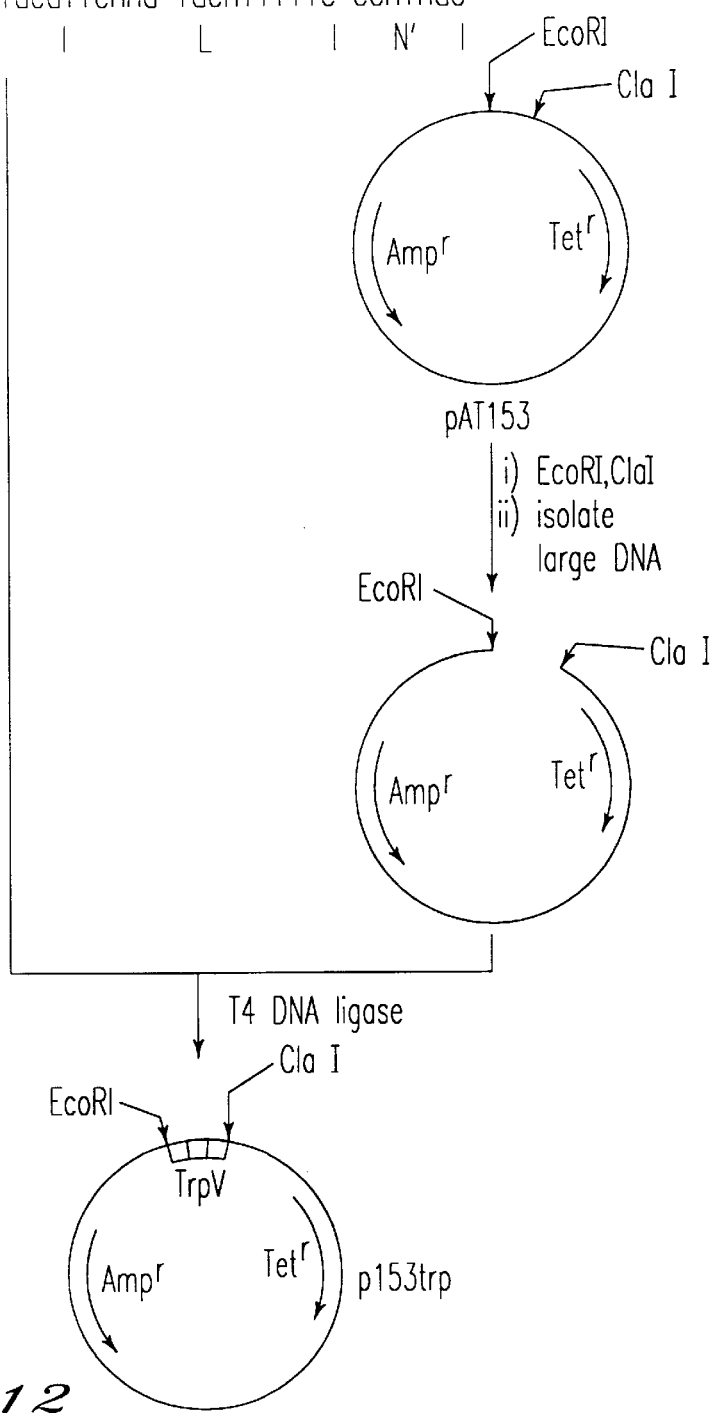
FIG. 12 is a schematic illustration of the construction protocol for the plasmid p153trp.

The 104 bp EcoRI-ClaI restriction fragment (20 ng) and the 3.6 bp EcoRI-ClaI restriction fragment (200 ng) were ligated with T4 DNA ligase (300 units) in a similar manner as described in Example 4 and the ligation mixture was used to transform *E. coli* JM 109. From one of the transformants, the desired plasmid p153trp containing the new promotor trpV was isolated and characterized by the restriction enzyme analysis. The schematic illustrations of the construction protocol for plasmid p153trp is shown in FIG. 12.

EXAMPLE 7

Construction of Plasmid pYS9121 p153trp (10 µg) was digested with SalI (10 units, Toyobo) and ClaI (10 units) and the approximately 2.9 kb restriction fragment was isolated by agarose gel electrophoresis. pYS9120A was digested with ClaI (10 units) and SalI (10 units) to isolate the approximately 1.3 kb restriction fragment.

Figure 13:
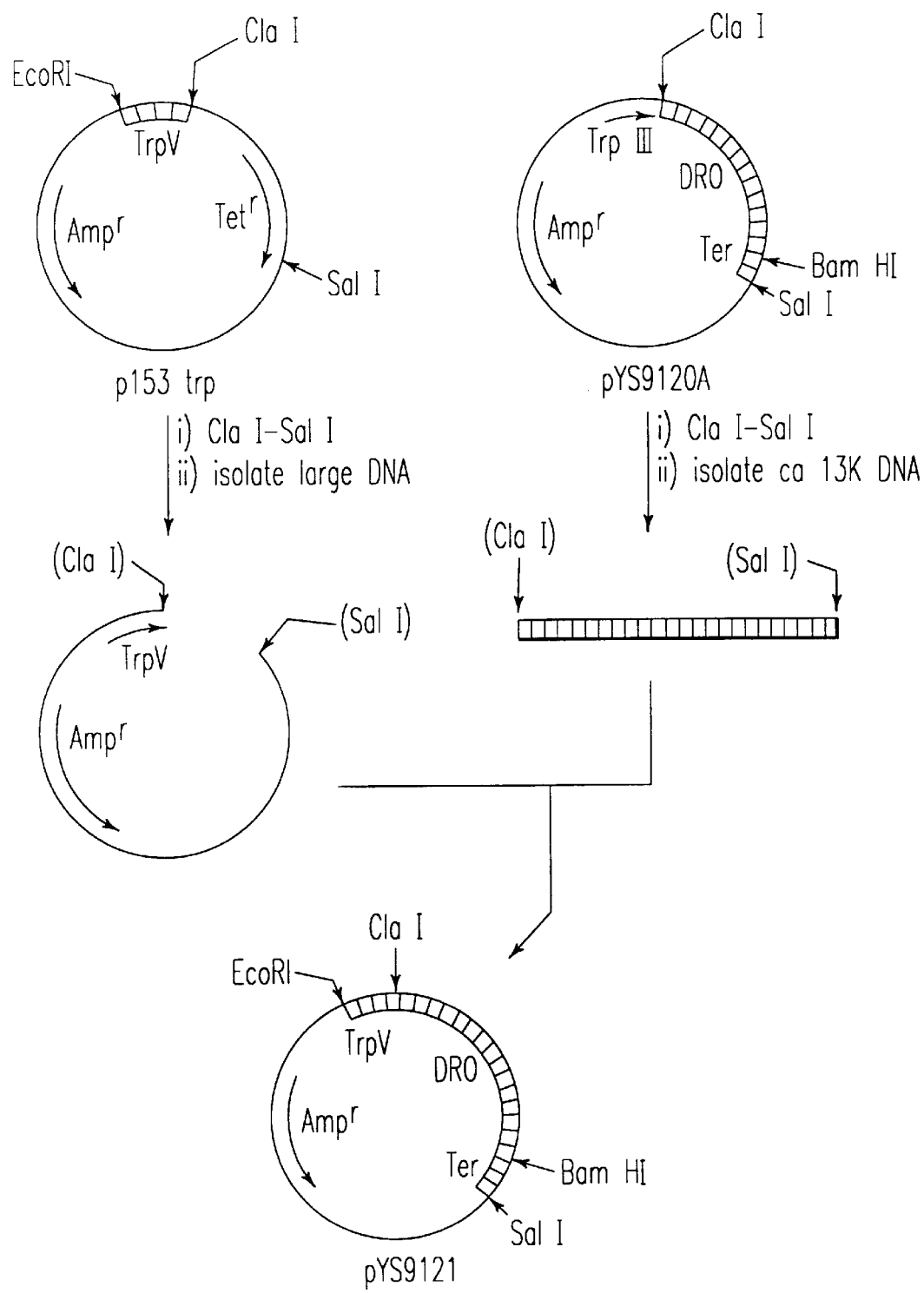
FIG. 13 is a schematic illustration of the construction protocol for the plasmid pYS9121.

The 2.9 bp ClaI-SalI restriction fragment (200 ng) and the 1.3 bp ClaI-SalI restriction fragment (20 ng) were ligated with T4 DNA ligase (300 units) and the ligation mixture was used to transform *E. coli* JM 109. From one of the transformants, the desired plasmid pYS121 was isolated and characterized. The schematic illustrations of the construction protocol for plasmid p153trp is shown in FIG. 13.

EXAMPLE 8

Construction of Plasmid pYS9122K pYS9121 (10 µg) was digested with EcoRI and SalI (10 units) to isolate the approximately 1.4 kb restriction fragment. pHSG298 (10 µg, Takara Shuzo) was digested with EcoRI (10 units) and SalI (10 units) to isolate the approximately 2.6 kb restriction fragment.

The 1.4 kb restriction fragment (50 ng) and the 2.6 kb restriction fragment (200 ng) were reacted in the presence of T4 DNA ligase (300 units). The ligation mixture was used to transform *E. coli* host cells, and the desired plasmid pYS9122K was isolated from the transformants in the conventionaly. The schematic illustrations of the construction protocol for plasmid pYS9122K is presented in FIG. 14.

EXAMPLE 9

Figure 15:
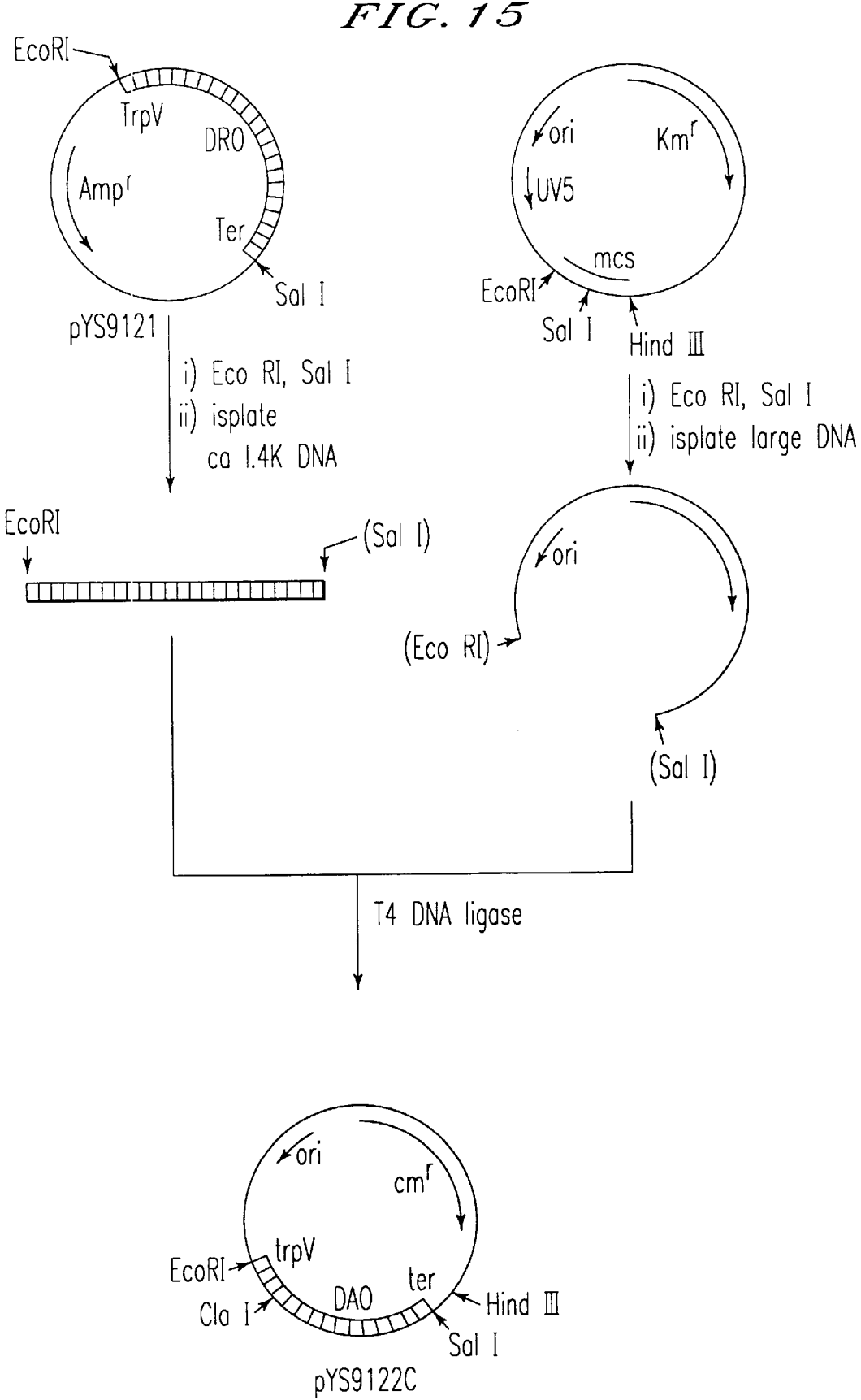
FIG. 15 is a schematic illustration of the construction protocol for the plasmid pYS9122C.

Construction of Plasmid pYS9122C pYS9122C was constructed in substantial accordance with the procedure of Example 8 from pYS9121 and pHSG396 (Takara Shuzo). The schematic illustrations of the construction protocol for plasmid pY9122C is presented in FIG. 15.

EXAMPLE 10

Cultivation of Transformant

A single colony of *E. coli* JM 109/pYS9122K (pYS9122C or pYS9120A) was grown in a 100 ml of L broth containing Km (50 µg/ml), [Cm (30 µg/ml) for *E. coli* JM 109/pYS9122C, Amp (50 µg/ml) for *E. coli* JM 109/pYS9120A] at 37° C. for 16 h. The resultant culture (0.8 ml) was mixed with 80% glycerol (0.2 ml) and stored at −8° C. (glycerol stock).

The glycerol stock was transferred to 100 ml of MS broth (0.2% glycerol, 1.2% Bactotrypton, 2.4% Yeast Extract, 0.11% Leu+Pro+Ile, 1.25% $K_2HPO_4$, 0.38% $K_2HPO_4$, 0.005% thiamine, HCl, 0.0493% $MgSO_4.7H_2O$, 0.003% $CaCl_2.2H_2O$, 0.0014% $FeSO_4.7H_2O$) containing 50 µg/ml of Km [Cm (30 µg/ml) or Amp (50 µg/ml), respectively] and cultivated at 30° C. for 16 h.

The resultant cultured broth (20 ml) was added to 350 ml of a modified M9CA broth of which components were substantially the same as those described in the literature [Maniatis, T. et al. (1982) "Molecular Cloning" Cold Spring Harbor Laboratory, p 440] except for that it contains 1% casamino acid (nitrogen source) and 1% glycerol (carbon source) and cultivated at 28° C. with shaking. After 10 hours culture, 50% glycerol (3.5 ml) and β-indoleacrylic acid (to the final concentration of 50 µg/ml) was added to the broth and the cultivation was continued for additional 22 h. The cells were harvested by centrifugation (5,000 rpm, 4° C., 10 min) and stored at −20° C.

EXAMPLE 11

Analysis and Assay

The frozen cells prepared from 20 ml of broth as described in Example 10 were suspended in 20 ml of TE [10 mM Tris-HCl (pH 8.0)-1 mM EDTA] and disrupted using a sonicator (US-600, Nihon Seiki) at 4° C. The suspension was centrifugated (15,000 rpm, 4° C., 10 min), and the recovered supernatant was used as the test sample.

i) Analysis by SDS-PAGE & Western Blot

SDS-PAGE analysis (15%) was performed according to the method described in the literature [Laemmli, U. K. (1970) Nature 227, 680–685]. Western blotting was performed by transferring proteins from polyacrylamide gel to a nitrocellulose membrane by electric elution, treating the membrane with rabbit anti DAO anti-serum (immunized against native DAO)-peroxidase labeled anti rabbit IgG, and visualizing with 4-chloro-1-naphthol-$H_2O_2$.

ii) Enzyme Activity Assay

DAO sample (0.1 ml) prepared as described above was mixed with 0.5 ml of sodium salt of cephalosporin C (20 µg/ml, adjusted to pH 7.5 with 1N NaOH) and 0.5 ml of 0.3M $KH_2PO_4$ (pH 8.0) and the mixture was incubated with shaking at 30° C. for 20 min. To the mixture was added $H_2O_2$ (1%; 0.1 ml), and the incubation was continued with shaking for additional 10 min. The reaction was interrupted by the addition of 4% AcOH (0.1 ml), which was followed by centrifugation and the supernatant were allowed to stand in ice. The supernatant was assayed for the DAO enzyme by HPLC. The unit definition is as follows. One unit is the amount of enzyme which catalyse the production of 1.0 µmole GL-7ACA per min from CCNa as the substrate.

HPLC conditions: column; Inertsil ODS-2 (4.6 mm×15 cm, Gaskuro Kogyo), pump; LC-6A (Shimadzu), detector; SPD-6A (Shimadzu), Recorder; CR-6A (Shimadzu), eluate; 3% acetonitril in 5% ammonium acetate. The results are shown in the following Table I.

TABLE I

Expression of recombinant DAO

| host E. coli | vector | A$_{600}$* | units/ml broth | units/ml broth/A$_{600}$ |
|---|---|---|---|---|
| JM109 | pYS9120A | 5.06 | 5.31 | 1.05 |
| JM109 | pYS9122C | 6.05 | 3.60 | 0.595 |
| JM109 | pYS9122K | 4.95 | 10.09 | 2.045 |

*The turbidity of the culture at the end of the cultivation.

EXAMPLE 12

Purification of Recombinant DAO

The frozen cells of *E. coli* JM 109/pYS9122K prepared from 350 ml broth in the same manner as described in Example 10 were suspended in 100 ml of 1 mM Tris.HCl (pH 8.0)-0.1 mM EDTA and dispersed by a sonicator. The supernatant was separated by centrifugation and the pellet was re-suspended in 100 ml of Tris.HCl buffer, sonicated and centrifuged to separate the supernatant. These procedures were repeated twice. The supernatants were combined and the pH was adjusted to pH 9.0 with 1N NaOH. To the resultant solution (310 ml) was added polyethylenimine to the final concentration of 0.01%, which was followed by the centrifugation at 4° C., 7,000 rpm for 40 min. To the supernatant (300 ml), was added 61.8 g of ammonium sulfate and the mixture was allowed stand for 16 hr at 4° C. and centrifuged at 4° C., 7000 rpm for 20 min.

The resultant supernatant (340 ml) was subjected to the hydrophobic column chromatography [resin; Toyopearl HW-65F (Toso), volume; 100 ml, column size; Pharmacia K26/40, eluate; 35% to 0% saturated ammonium sulfate in 1 mM Tris-HCl (pH 9.0)-0.1 mM EDTA (linear gradient), flow rate; 2.5 ml/min]. Collected fractions were analyzed by reversed phase HPLC [column; TSK gel octadecyl NPR (4.6 mm×3.5 cm, Toso), eluate; 0 to 60% acetonitril in 0.05% TFA (linear gradient over 10 min)]. Fractions (90 ml) containing activities were pooled and dialyzed against 5 liter of 20 mM ammonium acetate adjusted to pH 9.0 with 28% ammonium hydroxide. The dialyzed solution was subjected to the anion exchange chromatography [resin; DEAE Toy-pearl 650M (Toso), volume; 120 ml, column size; Pharmacia K26/40, eluate; 0 to 0.5M NaCl in 10 mM Tris-HCl (pH 9.0), linear gradient, flow rate; 2.5 ml/min]. Fractions containing the desired compound were pooled and combined (total 69 ml). The solution was dialyzed against 10 mM of PB (pH 9.0) to give purified recombinant DAO (r-DAO). The specific activity of purified r-DAO was 24.5 units per mg protein.

The pure r-DAO was further purified by reversed phase HPLC [column; Cosmosil 5C$_4$-300 (4.6 mm×7.5 cm, Cosmo Bio), eluate; 12 to 60% acetonitril in 0.005% TFA (linear gradient over 30 min)] in order to obtain DAO sample for the determination of the NH$_2$ terminal amino acid sequence. The N-terminal amino acid sequence of r-DAO was determined by 470 A peptide sequencer, Applied Biosystems and compared with that predicted from cDNA. These were identical as shown below.

cDNA (SEQ ID NO: 43) /M S$^1$ N T I V$^5$ V V G A G$^{10}$ V I G L T$^{15}$ rDAO (SEQ ID NO: 44)    S$^1$ N T I V$^5$ V V G A G$^{10}$ V I G L X$^{15}$ (X: uncertain amino acid)

The pure r-DAO gave a single band on SDS-PAGE and a comparison with standard proteins showed that the r-DAO has a molecular weight of 40,000±1,000 dalton on SDS-PAGE.

Cited Reference are:

1) T. Maniatis et al., Molecular Cloning, Cold Spring Harbor Laboratory, 1982

2) H. Okayama and P. Berg, Mol.Cell.Biol., 2, 161, 1982

3) D. Hanahan, J.Mol.Biol., 166, 557, 1983

4) M. W. Hunkapiller et al., Methods in Enzymology, 91, 399, 1983

5) M. W. Hunkapiller and L. E. Hood, Methods in Enzymology, 91, 486, 1983

6) C. L. Soliday et al., Proc.Nat.Acad.Sci.USA, 81, 3939, 1984

7) Inglia et al., Nucleic Acids Res., 9, 1627, 1982

8) R. W. Davis et al., Advanced Bacterial Genetics, p.174, Cold Spring Harbor Laboratory, 1980

9) E. M. Southern, J.Mol.Biol., 98, 116, 1975

10) E. M. Southern, J.Mol.Biol., 98, 503, 1975

11) J. Messing, Methods in Enzymology, 101, 20,

12) F. Sanger et al., Proc.Nat.Acad.Sci.USA, 74, 5463, 1977

13) S. Tabor and C. C. Richardson, Proc.Nat.Acad.Sci.USA, 84, 4767, 1987

---

---

We claim:

1. A process for using a DNA molecule which encodes a D-amino acid oxidase of *F. solani*, which comprises culturing a microorganism transformed by an expression vector comprising a nucleotide sequence having the sequence set forth in SEQ ID NO: 2 or which encodes a D-amino acid oxidase set forth in SEQ ID NO: 3, in an aqueous nutrient medium and recovering the D-amino acid oxidase from the resultant cultured broth.

2. A purified recombinant D-amino acid oxidase which is produced by the process of claim 1.

3. A process for preparing a compound of the formula (I):

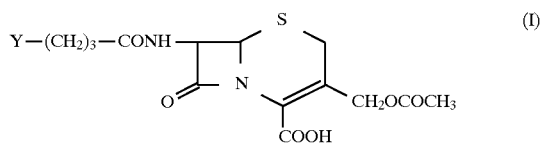

wherein Y is —COCOOH or —COOH or its salt which comprises contacting cephalosporin C or its salt with the cultured broth of a transformed microorganism comprising a nucleotide sequence having the sequence set forth in SEQ ID NO: 2 or which encodes a D-amino acid oxidase set forth in SEQ ID NO: 3, or a processed material derived from said broth.

4. The process of claim 1 wherein said transformed microorganism is *Escherichia coli*.

* * * * *